United States Patent
Flasinski et al.

(10) Patent No.: US 7,507,876 B2
(45) Date of Patent: Mar. 24, 2009

(54) EUKARYOTIC TRANSLATION INITIATION FACTOR GENE REGULATORY ELEMENTS FOR USE IN PLANTS

(75) Inventors: Stanislaw Flasinski, Chesterfield, MO (US); Steven E. Screen, St. Louis, MO (US); Deborah Feeney, Warrenton, MO (US); Richard Eric Cerny, Chesterfield, MO (US); Jessie Hart, Augusta, MO (US); Marianne Malven, Ellisville, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 11/743,923

(22) Filed: May 3, 2007

(65) Prior Publication Data

US 2007/0261133 A1 Nov. 8, 2007

Related U.S. Application Data

(62) Division of application No. 11/207,149, filed on Aug. 18, 2005, now Pat. No. 7,217,867.

(60) Provisional application No. 60/602,765, filed on Aug. 19, 2004.

(51) Int. Cl.
   *A01H 1/00* (2006.01)
   *C07H 21/04* (2006.01)
   *C12N 5/14* (2006.01)
   *C12N 15/09* (2006.01)

(52) U.S. Cl. .............. 800/298; 435/468; 435/419; 435/320.1; 800/300; 536/24.1

(58) Field of Classification Search .............. None
See application file for complete search history.

(56) References Cited

U.S. PATENT DOCUMENTS 5,362,865 A 11/1994 Austin ............. 536/24.1
5,530,196 A 6/1996 Fraley et al. ........... 800/298
5,641,876 A 6/1997 McElroy et al. ........ 536/24.1
5,659,122 A 8/1997 Austin ................ 800/317.3
6,051,753 A 4/2000 Comai et al. ........... 800/278

OTHER PUBLICATIONS

Kim et al. (Plant Molecular Biology, 24:105-117, 1994).*
Donald et al. (EMBO J. 9:1717-1726, 1990).*
Benfey et al., (Science 250:959-966, 1990).*
Mandel et al. (Plant Molecular Biology, 29:995-1004, 1995).*
Jiang et al. (Crop Science, 40:1729-1741, 2000).*
Christensen et al. (Transgenic Research, 5:213-218, 1996).*
Pautot et al. (Gene 77:133-140, 1989).*
Guarente et al. (TIG, 8:27-32, 1992).*
Maniatis et al. (Molecular Cloning: A Laboratory Manual, Cold Spring Harbor Laboratory, 1982).*
Brander et al.; "Highly conserved genes coding for eukaryotic translation initiation factor eIF-4A of tobacco have specific alterations in functional motifs," *Biochimica et Biophysica Acta*, 1261:442-444, 1995.
Database NCBI, GI:14594801, Database Accession No. AJ298137, Apr. 15, 2005.
Database NCBI, GI:475215, Database Accession No. X79008, Apr. 18, 2005.

* cited by examiner

*Primary Examiner*—Phuong T Bui
*Assistant Examiner*—Vinod Kumar
(74) *Attorney, Agent, or Firm*—Sonnenschein Nath & Rosenthal LLP

(57) ABSTRACT

The present invention provides eukaryotic translation initiation factor non-coding regulatory element polynucleotide molecules isolated from *Nicotiana tabacum*, *Arabidopsis thaliana*, and *Medicago truncatula* useful for modulating transgene expression in plants. The present invention also provides expression constructs containing the polynucleotide molecules useful for modulating transgene expression in plants. The present invention also provides transgenic plants and seeds containing the polynucleotide molecules useful for modulating transgene expression in plants.

18 Claims, 5 Drawing Sheets

SEQUENCE LISTING

<160> NUMBER OF SEQ ID NOS: 19

<210> SEQ ID NO 1
<211> LENGTH: 1054
<212> TYPE: DNA
<213> ORGANISM: Nicotiana tabacum

<400> SEQUENCE: 1

```
atcatgtata tttgtgcata tccatgaaaa tttgtgttat atatacgata tataatgtga      60
tacacatagg cgtccataaa agaattgtgt tgtatacacg atatacaaag tgatatacag     120
atgtccttaa aaatatgtgt gtgatataca ttgatgtaca caatatgcaa cgcgatatac     180
acatgtcaca gttggatttt aggtctgatg ttttacatga aatcagtcta aatcacttct     240
aatcttgctc aaattttgta tatagccccg tttaggtatt ttcaaccaat ttcactcaca     300
ccactcgttc aatctaacca aaaaaagaa gagagaagaa aaacaaagtt gaaatgaatt     360
tttctctctt agtttttgct tataattttt ctgattacct tttcaccccca ctgattttt     420 ttgcataatt tgcaaggatt tttgctaaac tatgagagcg aaagaaaaga gatagaagaa     480
gaaatacaag gagagaaagg gggagggacg cagtgaacaa aaaaagaagt tagcggcgaa     540 gaggggggggg gggggaagc agacggtttg gggccaattg tttgagagag aatatataag     600
agagtagttt ttttaggatt tggctatata atgtcaattt tttggggcta tcttttccta     660
acctaatata agactaaaaa attgtcaatt cctgttatgt gttatcacct ggtgccattt     720
tctcatagtt atacatatag tgaaaggaaa agagggtatt agtgccaatt ttgtaaagag     780
gttagaccta aattaggccc aagaggccca atagaaaatc tagccctcaa ttttgtggaa     840
```

| | |
|---|---|
| tccacgtcac cgacttcttg cattaccacc cgaagcggct ccgtattgat cctgtaactc | 900 |
| ccaatttcgg gtcaaaatag gaatttcaaa tacagaagcc aaaaaaaaaa ggaaagtaat | 960 |
| ccaaaacagt attcagaaag accataaaaa aacactagtc tcaatctttc tcttttcctc | 1020 |
| tttcctgaac tcctgcggcg tagatccgag gagt | 1054 |

<210> SEQ ID NO 2
<211> LENGTH: 94
<212> TYPE: DNA
<213> ORGANISM: Nicotiana tabacum

<400> SEQUENCE: 2

| | |
|---|---|
| ttcagacaaa accctaaccc cccaatcgct tttacccact tttcatttca ctctctcttt | 60 |
| cctattcctc agatcttttc ctcatctcta tcag | 94 |

<210> SEQ ID NO 3
<211> LENGTH: 892
<212> TYPE: DNA
<213> ORGANISM: Nicotiana tabacum

<400> SEQUENCE: 3

| | |
|---|---|
| gttagctatg ttttttttcc ctttaatatt ttaatgtatt tcttgtaata tttgtttgtg | 60 |
| tattgaagat tgaatcttga tgattgattg ttggtctgac tacagctggg ttttgtgtta | 120 |
| tgtaactatt tttaactatt ttggatagag gtctgtttga tgtgatgttc ttgattataa | 180 |
| aaataccatc ctactttgtt atctcatatc tggttggaac atgagcaatt tcatttctcc | 240 |
| tagttcttga attaaaaacc tgaaagtatt gtgcaaaaag atgctaggaa tgagactatc | 300 |
| attgttttga tgcaatatgt tcttttaagt aataggtgtt ttgtaagaag tctacgcagt | 360 |
| tctggatgta ttttactact cgggaaaact ggatagttgg atacttatta tgtataggaa | 420 |
| gtaaatgtgg ggattataat gcctttctct gccatctgct ctttgtattt tgtgtaaagc | 480 |
| ttggcatgcc tctcgtcaga tagccatcgc taccgtacat tcttttaaga atgaagcact | 540 |
| tagacacttg ctcgtttctg cctttgtcac attgacccag catcatataa tctgaaagat | 600 |
| tggttagcag ttggctgcta tttaacttgt atgttaaaac aattgatttt catgtgtatc | 660 |
| tcctcctttt gtgctttgtg cttcttcata aaagaaagaa aacatacatt cggttgtgct | 720 |
| ctcctccttt ttcaatggta gagaggaaga acagataatt ttattgctgc tgtaggtatt | 780 |
| tgacatctgt gatattttca tagtaaggtt ttgtttttc cttttatttt agttcaagat | 840 |
| tgtttcatga atttccataa gcgtaatacc atagttcttt tatttgctac ag | 892 |

<210> SEQ ID NO 4
<211> LENGTH: 918
<212> TYPE: DNA
<213> ORGANISM: Arabidopsis thaliana

<400> SEQUENCE: 4

| | |
|---|---|
| gcttcacaaa tttcggtttg tactttatta tattgggccc tattattatt ctctgagctt | 60 |
| ttgcgtctca ccaaaagaca gagatcatca ggtgcgttag tgattacgta ggcatctaat | 120 |
| gaacggcagg gattagtcaa acttattaat gggcctaatc tttggcccat cgttttccct | 180 |
| cgattcctgt cacacaaaaa actcctagct cttcctctac ctacacaagc taaatacata | 240 |
| ttttttgctt atcctaagca tcatgattat gttttgccct ctccagcttt ttcttcaatg | 300 |
| gcaacagatt ctaagaaagt ctcttgaggc taaaatcaaa gcattttttg ttgaagatag | 360 |

| | | | |
|---|---|---|---|
| atagcaactt | gctgcttctt | catactagct agttaccttc ttcttactca atgtgttttg | 420 |
| cttcgtttca | aggattcttc | atatcacttg tggaacaatt acatgattaa acattcaaca | 480 |
| tagagagata | gatgtgttaa | taagtaaaga cattttcaga taaaacgttc ttatcagtca | 540 |
| ctttattctt | ctaatatcct | cgttgtaatc gggaaaatgc tttgtaacgt caaaaagcaa | 600 |
| taaaagttgc | aggagaaaga | aagctttgga aaagaaaata aaataaatga agaatatttt | 660 |
| ctttgctagt | cacaaaataa | atgaagaatt tatgttccta atttcccact agatatttgt | 720 |
| ttatttattt | ttgccaaaat | caagttaaga caatgagcta agtgttggaa aaccttgtcc | 780 |
| gagccaaaag | agtaaaaaga | aagggaataa aggggtaaaa ccggaaatcc gaaaagaaa | 840 |
| aggagaagat | ttccaaagga | gaaaaccccta aagacggagt atataaacaa ggtaacgcgt | 900 |
| tttctctcag | cctctttc | | 918 |

<210> SEQ ID NO 5
<211> LENGTH: 135
<212> TYPE: DNA
<213> ORGANISM: Arabidopsis thaliana

<400> SEQUENCE: 5

| | | | |
|---|---|---|---|
| ggatattcca | ccagtctctc | gcaatcttcg ctcttctctt tgctctctct ctctcaacgc | 60 |
| ggttcagatc | cgagtttggg | agattcaagc tccctgaaaa aagcccttta ctctcgctta | 120 |
| ccaactttgc | tccag | | 135 |

<210> SEQ ID NO 6
<211> LENGTH: 647
<212> TYPE: DNA
<213> ORGANISM: Arabidopsis thaliana

<400> SEQUENCE: 6

| | | | |
|---|---|---|---|
| gttcgcatcc | tatcggattg | tctatctatt atctcgatgt aacttttacg attcatgatt | 60 |
| gtttctttac | ttttggattg | ttctgatttg ttttttttgtg ttttccgata gatttggttt | 120 |
| caactttgtt | gagttgattt | ggaagttttg atttttcgtt acttcaagat cgttttttt | 180 |
| gctgtggaag | tgctttcgtt | tttgttctct ttattagatt ctgagctgct gatgatgacg | 240 |
| attattaaat | ttaggatcta | cacatctgta gatttgttga tgggtttgta gattttgtta | 300 |
| cggctaggtt | agtctctcaa | tagaatgaaa tgaatcgtct tcaaagctca gatgttcttg | 360 |
| tcttaacact | cacttggttt | tgtctgattg aatgttttt tttgtaattt ggagaaatag | 420 |
| gttgagtggt | gtctatgttt | aatagataac catatgtgcc tttatacatt ttctccgcac | 480 |
| atcatctgag | gcagatatta | atgcttgttt tcctctcttt atggacttcg agtttggctt | 540 |
| tcttgtcaca | tttcctcctt | tgcaatcata ttattaacga tatcaaaata ggtgttgtct | 600 |
| ctcttccttt | tgatatgaaa | tctgattgtt ttgttctttt tatgtag | 647 |

<210> SEQ ID NO 7
<211> LENGTH: 1941
<212> TYPE: DNA
<213> ORGANISM: Medicago truncatula

<400> SEQUENCE: 7

| | | | |
|---|---|---|---|
| cgtcttgtgt | gatatctaac | atccactttg ggtgcgtttg ttgtagattt caacaaaata | 60 |
| gattttatgt | tagaaaaatt | agagattctt gtttagataa tttgaaaaaa ttttgaagct | 120 |
| atttgtgttt | ttttattatc | caaaaaaatc gcttttttga aaaaaatgat ttttaaatag | 180 |
| tttatgtctt | tcccccttat | gtttaaaaaa atagattttg agaaaagcta atcctaatag | 240 |

-continued

```
tttttttattt tagagtcaaa atatttttttt ttttgataaa gtaaatctttt ttaaaatcct     300 aaacaaacac tcaaaactga caagtaatttt ttttttaataa aaaatctaaa acaaatgtgc     360
ctttatgtca ccgtaaaaga caaaggaatt gttctcgtga gcttagttca gttggtatgg     420
acaatgcata aaatatgcca gatccatggt tcaattacat tgttgtcctt gttagccgat     480
cttagttttt atagtgagaa aagcttcaat tttttttttt aaattctctt tttctttccg     540
tcattgagga atggatgatt ttaggttatt tttgacttaa aatcattttt atgcgtcttt     600
ttctcatttc tttcgatcta aataagtgat ttttacatat atcaagtttt tcttgtgtt     660 tttcataaca gatcaacaca gcaacacagg aggtcaaaaa atagtcccac caccaaacta     720
atcattatat aataaggata ttttagaagg atgactcacg tggatcaaaa tttgagttaa     780
atagtttaac ttcagtccat tatgttctcc tgaaattcca aataaaaaga ttaagtattt     840
atcccatcag ttgaaaattg ataaaaacaa ccaattagtt taccaaggct aaagtatgag     900
ctattgaacc ccgccaaagc taatctagtt agacaaatca acaaattcca atttacaaca     960
caaccctaat gcctcccta taaaaagtca ccccaatttt acacttcaat agaaaatgac    1020
ccaatacttg gaaccaaaac acctccattg aatgagccaa tacttcaata gaagaaagtt    1080
atgtaactga aatagaataa ttaactcata aaattaatgt aaaaccaatt caagttttct    1140
acatttgaca ccttttgtac aaaatggtaa aaccaaattg gaaagtgaca acatgaaaaa    1200
tataatttga tcacatattc ttccaataat aaaggtgatg gactgacatc attttcaaat    1260
ctctctctaa agttctagta aatgtcagtt agtaaactaa cctctgtttt tcaaatcttt    1320
ctccaaaata ctcaagtgtc aatcactaaa taaaaaccaa agattttcct acaaacatta    1380
tagccaacct aaaacgaagt ataaattata cttggacaca aacagagtgc aaaagataaa    1440
ttagacaaag atccatttaa attaatgtgc tgaataatta tgaagcaaga tatcaaaatc    1500
aaattagata aaagtgtgag tggtgaattt ctcacagttt ataaaatcat caaactcgaa    1560
agcctagttt tatataagct aaggacgatt cttaaatacc aaaaaaataa ataaaaacca    1620
agaaagatta agaaatatt tctctgagtt ttacactgtt attaaggata tttggatccg    1680
atgataaaag ttttcattca acttaattat aggtccttga tacgaatcca actttacatt    1740
atgataaatc ttttaaagaa tagttttacc atcgattatt gttccacccg gttcaagaat    1800
tttagaggat actcagataa aataaaataa aaataaaata tgaaactatt ggtattttag    1860
agattaaaac taaattttgt gttttttggg ggtgtaatca gcaaatccta atcctagtag    1920
tagtaaaaat acatacgcta c                                                1941
```

```
<210> SEQ ID NO 8
<211> LENGTH: 1484
<212> TYPE: DNA
<213> ORGANISM: Medicago truncatula

<400> SEQUENCE: 8
```

```
cattgttgtc cttgttagcc gatcttagtt tttatagtga gaaaagcttc aattttttttt      60 tttaaattct cttttctttt ccgtcattga ggaatggatg attttaggtt attttttgact     120 taaaatcatt tttatgcgtc tttttctcat ttctttcgat ctaaataagt gattttttaca     180 tatatcaagt tttttcttgt gttttttcata acagatcaac acagcaacac aggaggtcaa     240
aaaatagtcc caccaccaaa ctaatcattg tataataagg atattttaga aggatgactc     300
acgtggatca aaatttgagt taaatagttt aacttcagtc cattatgttc tcctgaaatt     360
```

```
ccaaataaaa agattaagta tttatcccat cagttgaaaa ttgataaaaa caaccaatta      420
gtttaccaag gctaaagtat gagctattga accccgccaa agctaatcta gttagacaaa      480
tcaacaaatt ccaatttaca acacaaccct aatgcctccc ttataaaaag tcaccccaat      540
tttacacttc aatagaaaat gacccaatac ttggaaccaa aacacctcca ttgaatgagc      600
caatacttca atagaagaaa gttatgtaac tgaaatagaa taattaactc ataaaattaa      660
tgtaaaacca attcaagttt tctacatttg acacctttg tacaaaatgg taaaaccaaa       720
ttggaaagtg acaacatgaa aaatataatt tgatcacata ttcttccaat aataaaggtg      780
atggactgac atcattttca atctctctc taaagttcta gtaaatgtca gttagtaaac       840
taacctctgt ttttcaaatc tttctccaaa atactcaagt gtcaatcact aaataaaaac      900
caaagatttt cctacaaaca ttatagccaa cctaaaacga agtataaatt atacttggac      960
acaaacagag tgcaaaagat aaattagaca aagatccatt taaattaatg tgctgaataa     1020
ttatgaagca agatatcaaa atcaaattag ataaaagtgt gagtggtgaa tttctcacag     1080
tttataaaat catcaaactc gaaagcctag ttttatataa gctaaggacg attcttaaat     1140
accaaaaaaa taaataaaaa ccaagaaaga ttaagaaata ttttctctga gttttacact     1200
gttattaagg atatttggat ccgatgataa aagttttcat tcaacttaat tataggtcct     1260
tgatacgaat ccaactttac attatgataa atcttttaaa gaatagtttt accatcgatt     1320
attgttccac ccggttcaag aattttaggg gatactcaga taaaataaaa taaaaataaa     1380
atatgaaact attggtattt tagagattaa aactaaattt tgtgttttt gggggtgtaa      1440 tcagcaaatc ctaatcctag tagtagtaaa aatacatacg ctac                      1484

<210> SEQ ID NO 9
<211> LENGTH: 1029
<212> TYPE: DNA
<213> ORGANISM: Medicago truncatula

<400> SEQUENCE: 9
gccaaagcta atctagttag acaaatcaac aaattccaat ttacaacaca accctaatgc       60
ctcccttata aaagtcacc ccaattttac acttcaatag aaaatgaccc aatacttgga       120
accaaaacac ctccattgaa tgagccaata cttcaataga agaaagttat gtaactgaaa      180
tagaataatt aactcataaa attaatgtaa aaccaattca gttttctac atttgacacc       240 ttttgtacaa aatggtaaaa ccaaattgga aagtgacaac atgaaaaata taatttgatc      300
acatattctt ccaataataa aggtgatgga ctgcatcat tttcaaatct ctctctaaag       360
ttctagtaaa tgtcagttag taaactaacc tctgttttc aaatctttct ccaaaatact       420
caagtgtcaa tcactaaata aaaccaaag atttttcctac aaacattata gccaacctaa      480
aacgaagtat aaattatact tggacacaaa cagagtgcaa aagataaatt aggcaaagat     540
ccatttaaat taatgtgctg aataattatg aagcaagata tcaaaatcaa attagataaa      600
agtgtgagtg gtgaatttct cacagtttat aaaatcatca aactcgaaag cctagtttta     660
tataagctaa ggacgattct taaataccaa aaaataaat aaaaaccaag aaagattaag       720
aaatattttc tctgagtttt acactgttat taaggatatt tggatccgat gataaaagtt     780
ttcattcaac ttaattatag gtccttgata cgaatccaac tttacattat gataaatctt     840
ttaaagaata gttttaccat cgattattgt tccacccggt tcaagaattt tagaggatac      900
tcagataaaa taaataaaa ataaaatatg aaactattgg tatttagag attaaaacta       960 aatttttgtgt ttttgggggg tgtaatcagc aaatcctaat cctagtagta gtaaaaatac    1020
``` atacgctac 1029

<210> SEQ ID NO 10
<211> LENGTH: 156
<212> TYPE: DNA
<213> ORGANISM: Medicago truncatula

<400> SEQUENCE: 10
aaataaaaag cacgcatata taacctaaat ctctctctca ctcttccctt caactccacg    60
gcgcagatcc gaggagtttg ggaaaccta attttcaatc tttcttcgat cttcttctcg    120
cttcaattct ctcttcttca ctcactccac aagcag    156

<210> SEQ ID NO 11
<211> LENGTH: 647
<212> TYPE: DNA
<213> ORGANISM: Medicago truncatula

<400> SEQUENCE: 11
gtatacgtat ctcaattctc aatttctccc aattttcat tcttttagat tttaatctgc    60 tttttacct ttaaattatg aacttttat tttgaatcta agtttgatct gattgctttt    120
ttattaataa tatattaaag ttctgatctt gaaatcaat tatgattaac aaaaaaaag    180 tcgatttta ttatttgttg cttatgattt gccctatgca gttgcatata aaagttatga    240
tttttgaaat cagttatgat taacataaaa acaaaaatca attttttattg ttattttgtt    300 atgattcgtt gtatagagtt tgaatttaag atttgattca tgtcttagag gatttgttgt    360
tttctgattg gtgctttttc atgtgtttat gttatgtatt gtaatgtttg aagctgtttt    420
tttatgattt atttgtgcat ctgtcttgtt cgtgaaattc tatttttttt tttataaatc    480
atgtaattaa aattcatagc tttgcttaga acagcctttg tattatgtgt tttcttgtcg    540
tgatatttgg gatgtctttt gttggtggtt ttattttgtt tgaaaatatg ttcttttttgt    600 tatatatctg ttgaatttta cctaaagtgt gttgtttgt tctatag    647

<210> SEQ ID NO 12
<211> LENGTH: 28
<212> TYPE: DNA
<213> ORGANISM: Artificial Sequence
<220> FEATURE:
<223> OTHER INFORMATION: Synthetic oligonucleotide primer

<400> SEQUENCE: 12
ctagtcccgg gatcatgtat atttgtgc    28

<210> SEQ ID NO 13
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 13
ccttccggtg ccaagccagc catggctgta g    31

<210> SEQ ID NO 14
<211> LENGTH: 40
<212> TYPE: DNA
<213> ORGANISM: Artificial Sequence
<220> FEATURE:
<223> OTHER INFORMATION: Synthetic oligonucleotide primer

```
<400> SEQUENCE: 14
gatcgatcag cggccgcttc acaaatttcg gtttgtactt                              40

<210> SEQ ID NO 15
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 15
atcctgccat ggatgctaca taaaaagaac aaaacaatca                              40

<210> SEQ ID NO 16
<211> LENGTH: 39
<212> TYPE: DNA
<213> ORGANISM: Artificial Sequence
<220> FEATURE:
<223> OTHER INFORMATION: Synthetic oligonucleotide primer

<400> SEQUENCE: 16
gatcagatct gcggccgcgt cttgtgtgat atctaacat                               39

<210> SEQ ID NO 17
<211> LENGTH: 40
<212> TYPE: DNA
<213> ORGANISM: Artificial Sequence
<220> FEATURE:
<223> OTHER INFORMATION: Synthetic oligonucleotide primer

<400> SEQUENCE: 17
gatcagatct gcggccgcat tgttgtcctt gttagccgat                              40

<210> SEQ ID NO 18
<211> LENGTH: 37
<212> TYPE: DNA
<213> ORGANISM: Artificial Sequence
<220> FEATURE:
<223> OTHER INFORMATION: Synthetic oligonucleotide primer

<400> SEQUENCE: 18
gatcagatct gcggccgcca aagctaatct agttaga                                 37

<210> SEQ ID NO 19
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 19
aacctgacat gtgactatag aacaaaacaa cacact                                  36
```

US 7,507,876 B2

EUKARYOTIC TRANSLATION INITIATION FACTOR GENE REGULATORY ELEMENTS FOR USE IN PLANTS

This application is a divisional application of U.S. application Ser. No. 11/207,149 (now U.S. Pat. No. 7,217,867), filed Aug. 18, 2005, which claims the benefit under 35 USC § 119(e) of United States provisional application Ser. No. 60/602,765 filed Aug. 19, 2004, the disclosures of which are each herein incorporated by reference in their entirety.

INCORPORATION OF SEQUENCE LISTING

Two copies of the sequence listing (Seq. Listing Copy 1 and Seq. Listing Copy 2) and a computer-readable form of the sequence listing, all on CD-ROMs, each containing the file named pa_01078.rpt, which is 14,336 bytes (measured in MS-DOS) and was created on Aug. 17, 2005 are hereby incorporated by reference.

FIELD OF THE INVENTION

The invention relates to the fields of plant molecular biology and plant genetic engineering, and comprises polynucleotide molecules useful for the expression of transgenes in plants.

BACKGROUND

One of the goals of plant genetic engineering is to produce plants with agronomically desirable characteristics or traits. The proper expression of a desirable transgene in a transgenic plant is one way to achieve this goal. Regulatory elements such as promoters, leaders, and introns are non-coding polynucleotide molecules which play an integral part in the overall expression of genes in living cells. Isolated regulatory elements that function in plants are therefore useful for modifying plant phenotypes through the methods of genetic engineering.

Many regulatory elements are available and are useful for providing good overall expression of a transgene. For example, constitutive promoters such as P-FMV, the promoter from the 35S transcript of the Figwort mosaic virus (U.S. Pat. No. 6,051,753); P-CaMV 35S, the promoter from the 35S RNA transcript of the Cauliflower mosaic virus (U.S. Pat. No. 5,530,196); P-Rice Actin 1, the promoter from the actin 1 gene of *Oryza sativa* (U.S. Pat. No. 5,641,876); and P-NOS, the promoter from the nopaline synthase gene of *Agrobacterium tumefaciens* are known to provide some level of gene expression in most or all of the tissues of a plant during most or all of the plant's lifespan. While previous work has provided a number of regulatory elements useful to affect gene expression in transgenic plants, there is still a great need for novel regulatory elements with beneficial expression characteristics. In particular, there is a need for regulatory elements that are capable of directing expression of transgenes in transgenic crop plants at high levels and in particular tissues, organs, or during specific developmental stages of plant growth. Many previously identified regulatory elements fail to provide the patterns or levels of expression required to fully realize the benefits of expression of selected genes in transgenic plants.

Eukaryotic translation initiation factor eIF-4A is an ATP-dependent RNA helicase protein that is required for the binding of mRNA to ribosomes. Members of this family have been reported in many species including mouse, *Drosophila*, yeast, tobacco, *Arabidopsis*, wheat, and rice (K A Brander, et al. (1995) *Biochimica et Biophysica Acta* 1261:424-444). We hypothesized that a promoter and other non-coding regulatory elements from an eIF-4A gene would have a constitutive expression pattern and that the promoter and regulatory elements would be useful to direct expression of a transgene such as a glyphosate resistant 5-enolpyruvylshikimate-3-phosphate synthase (EPSPS) transgene to produce a glyphosate tolerant plant. The efficient production of glyphosate tolerant plants requires the use of a promoter and regulatory elements capable of directing transgene expression in all tissues including the most sensitive reproductive organs such as anthers and meristem tissues. The present invention thus provides such promoters and regulatory elements isolated from the eukaryotic translation initiation factor (eIF4A) genes of *Nicotiana tabacum, Arabidopsis thaliana,* and *Medicago truncatula*.

SUMMARY

In one embodiment the invention provides promoters and regulatory elements isolated from *Nicotiana tabacum, Arabidopsis thaliana,* and *Medicago truncatula*, provided as SEQ ID NO: 1-11 useful for modulating transgene expression in plants. In another embodiment the invention provides constructs comprising the promoter and regulatory elements useful for modulating transgene expression in plants. In another embodiment the invention provides a transgenic plant containing the promoter and regulatory elements operably linked to a heterologous DNA molecule and the seed of the transgenic plant. The transgenic plant expresses an agronomically desirable phenotype, in particular herbicide tolerance, more specifically, tolerance to glyphosate herbicide.

DETAILED DESCRIPTION

Figure 1:
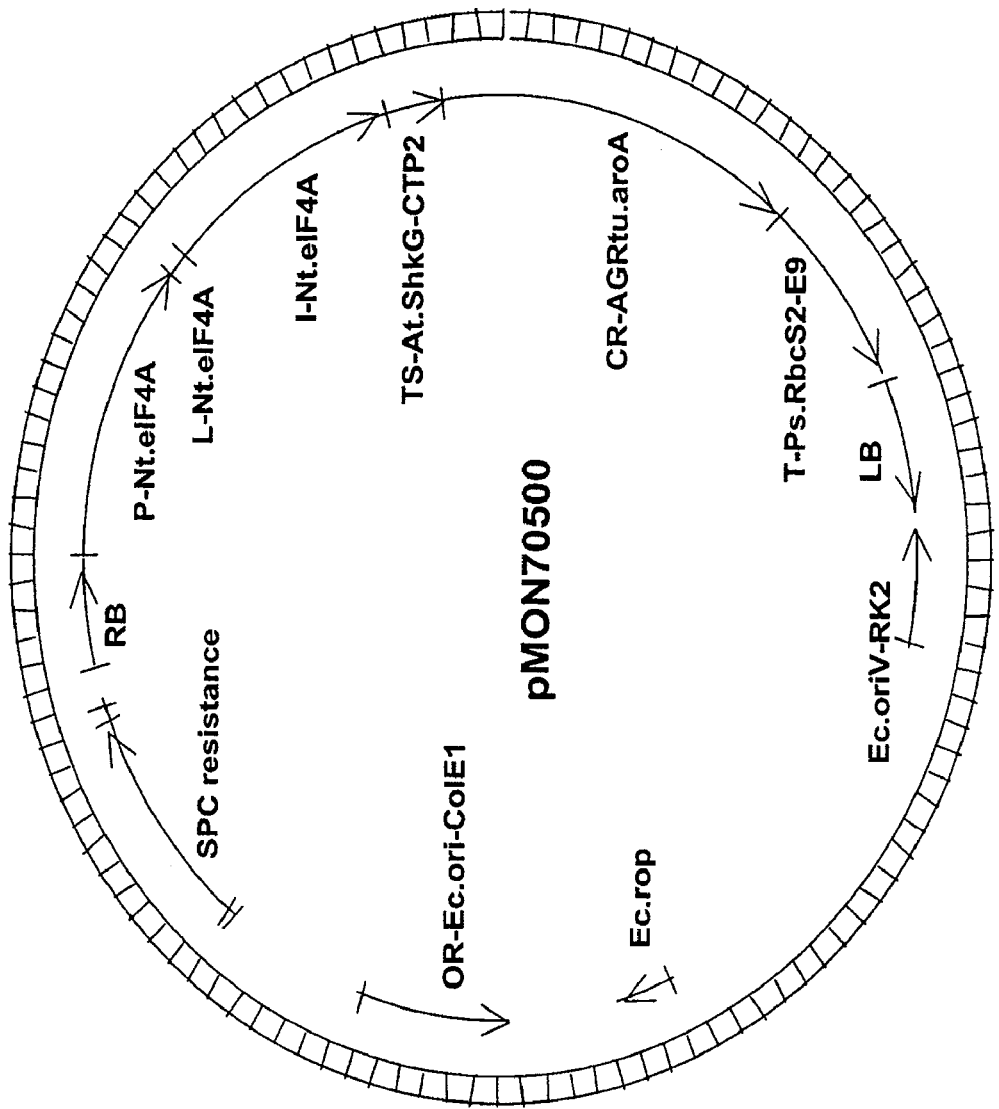
FIG. 1 represents pMON70500.
Figure 2:
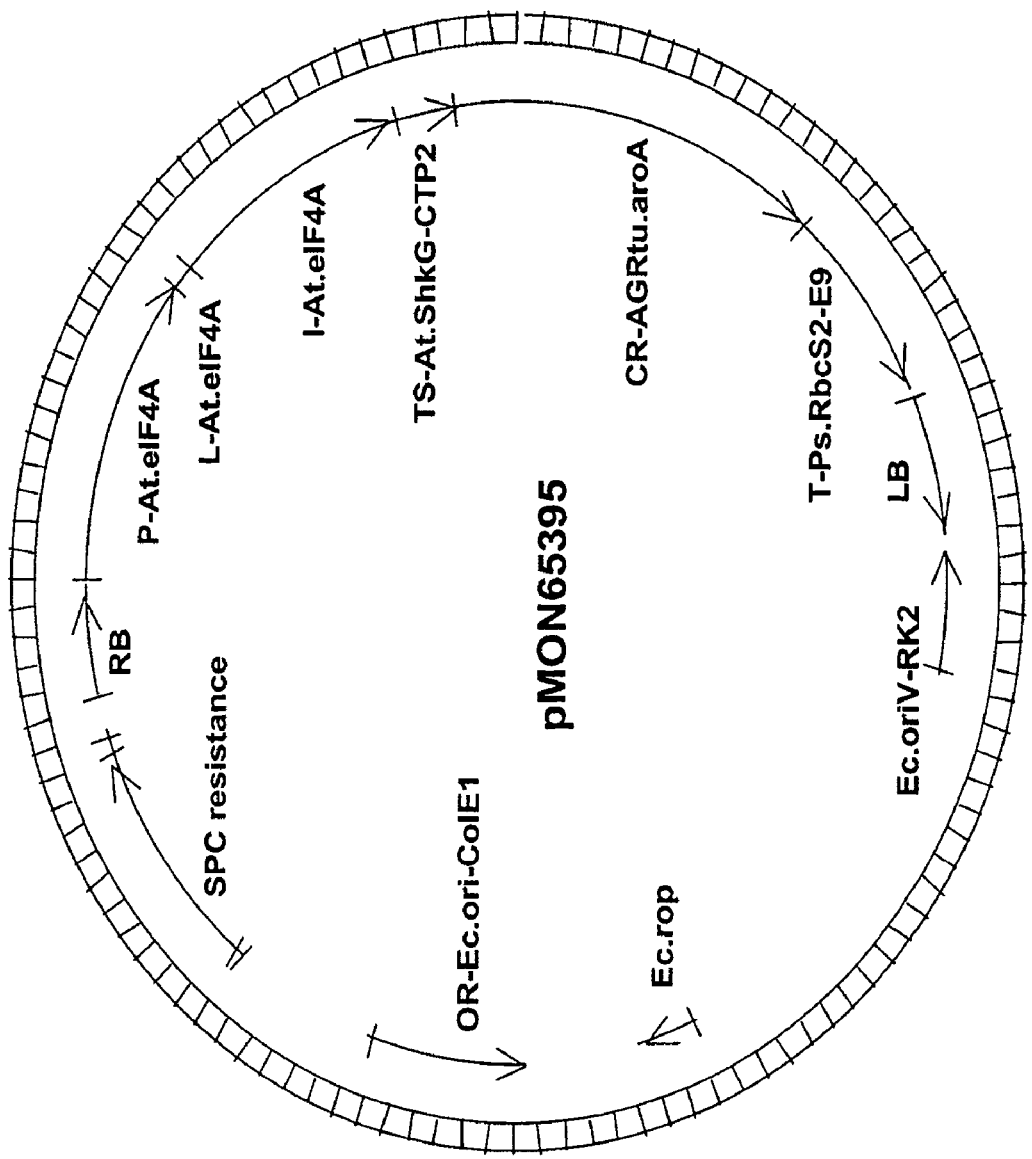
FIG. 2 represents pMON65395.
Figure 3:
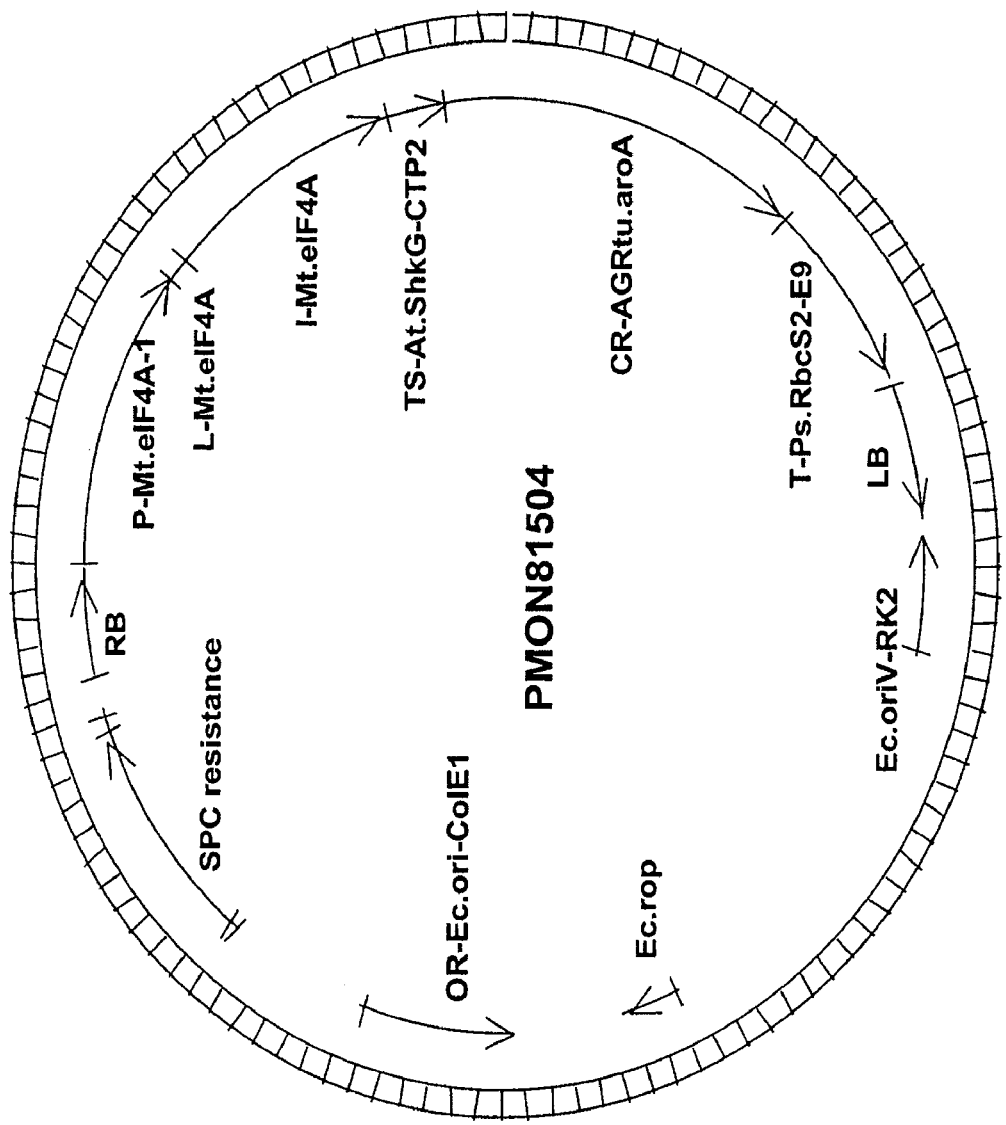
FIG. 3 represents pMON81504.
Figure 4:
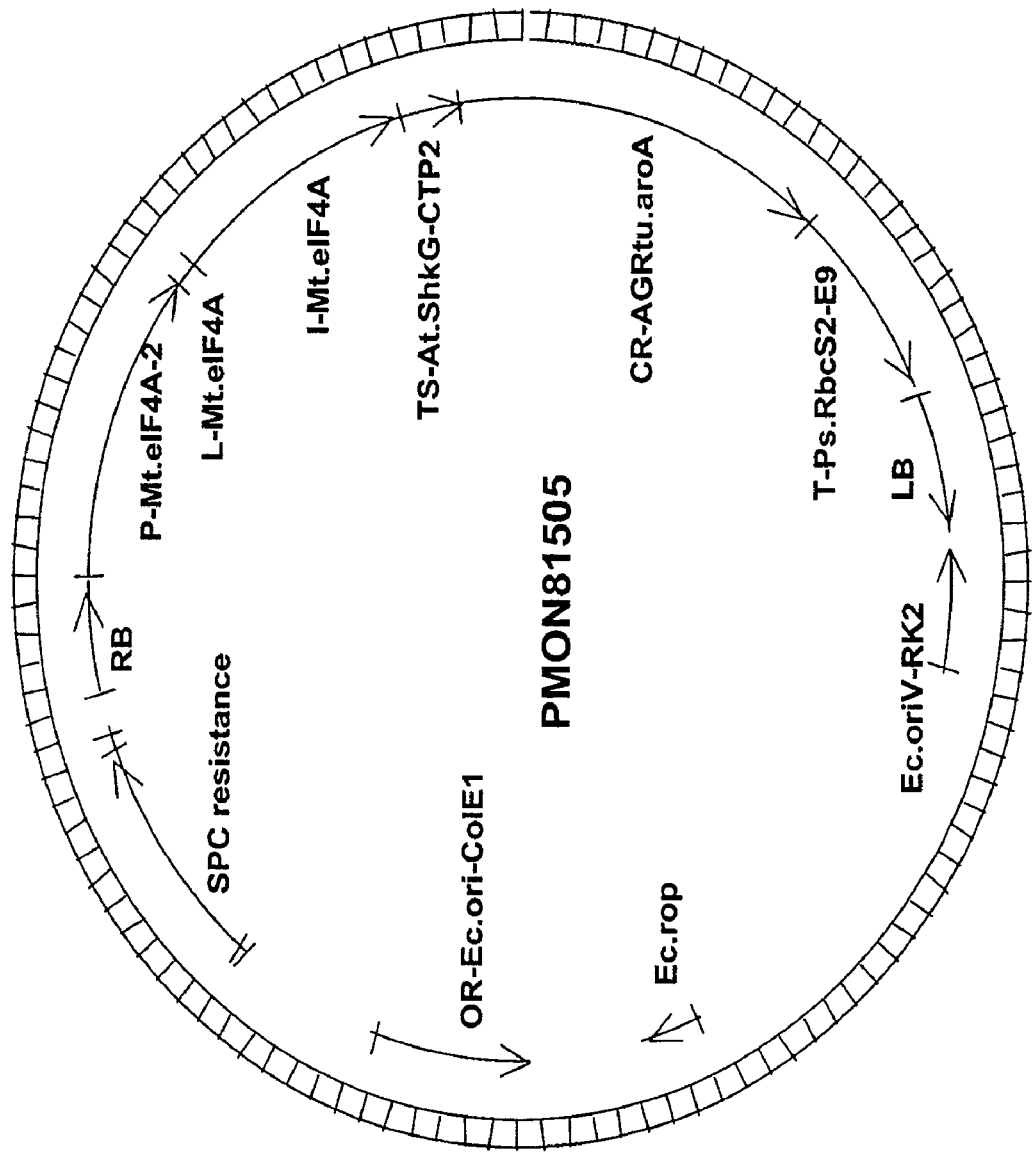
FIG. 4 represents pMON81505.
Figure 5:
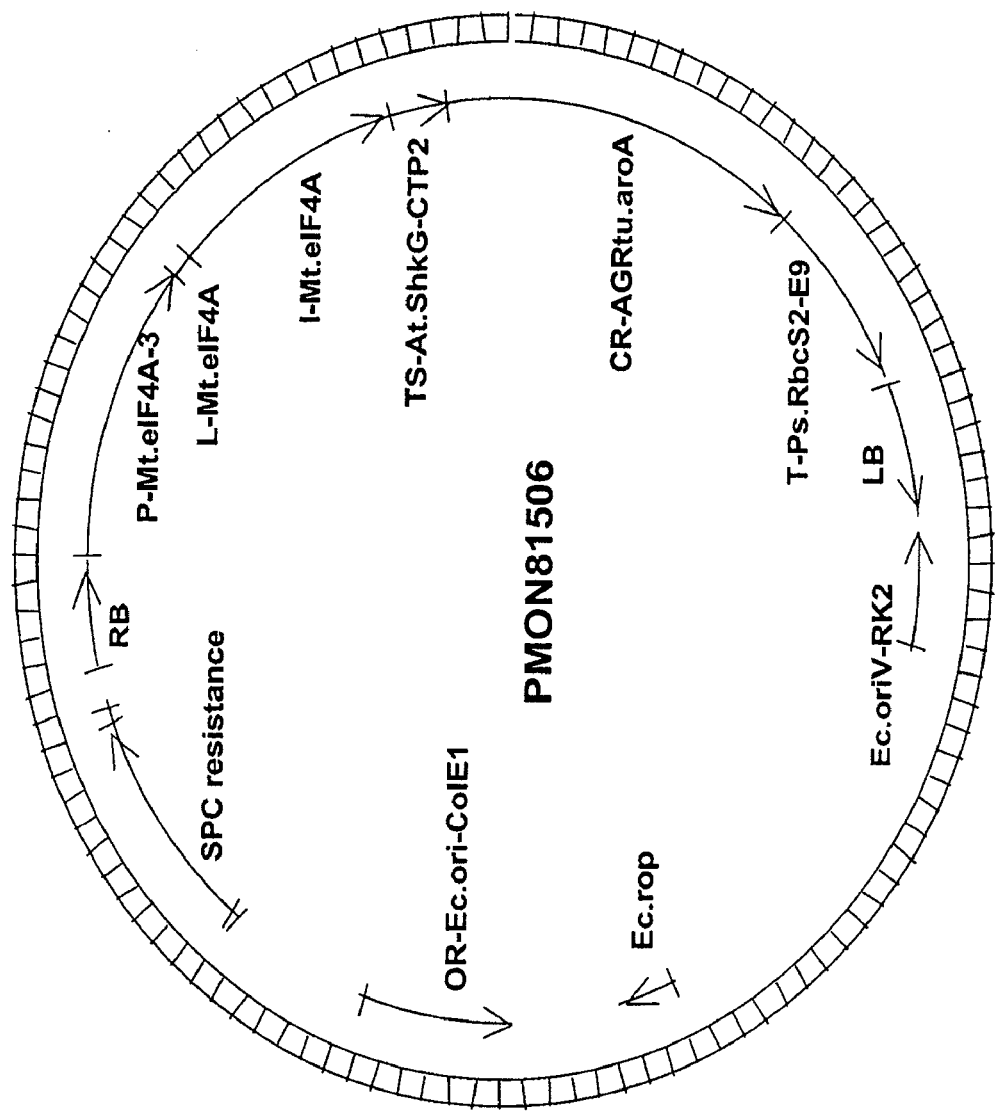
FIG. 5 represents pMON81596.

The invention disclosed herein provides polynucleotide molecules having gene regulatory activity from *Nicotiana tabacum, Arabidopsis thaliana,* and *Medicago truncatula*. The design, construction, and use of these polynucleotide molecules are one object of this invention. The polynucleotide sequences of these polynucleotide molecules are provided as SEQ ID NO: 1-11. These polynucleotide molecules are capable of affecting the transcription of operably linked transcribable polynucleotide molecules in both vegetative and reproductive tissues of plants and therefore can selectively regulate expression of transgenes in these tissues.

Definitions

The following definitions and methods are provided to better define the present invention and to guide those of ordinary skill in the art in the practice of the present invention. Unless otherwise noted, terms are to be understood according to conventional usage by those of ordinary skill in the relevant art.

As used herein, the term "fragment" or "fragment thereof" refers to a finite polynucleotide sequence length that comprises at least 50, at least 75, at least 85, or at least 95 contiguous nucleotide bases wherein its complete sequence in entirety is identical to a contiguous component of the referenced polynucleotide molecule.

As used herein, the term "polynucleotide molecule" refers to the single- or double-stranded DNA or RNA molecule of genomic or synthetic origin, i.e., a polymer of deoxyribonucleotide or ribonucleotide bases, respectively, read from the 5' (upstream) end to the 3' (downstream) end.

As used herein, the term "polynucleotide sequence" refers to the sequence of a polynucleotide molecule. The nomenclature for nucleotide bases as set forth at 37 CFR § 1.822 is used herein.

As used herein, the term "regulatory element" refers to a polynucleotide molecule having gene regulatory activity, i.e. one that has the ability to affect the transcription or translation of an operably linked transcribable polynucleotide molecule. Regulatory elements such as promoters, leaders, introns, and transcription termination regions are non-coding polynucleotide molecules having gene regulatory activity which play an integral part in the overall expression of genes in living cells. Isolated regulatory elements that function in plants are therefore useful for modifying plant phenotypes through the methods of genetic engineering. By "regulatory element" it is intended a series of nucleotides that determines if, when, and at what level a particular gene is expressed. The regulatory DNA sequences specifically interact with regulatory proteins or other proteins.

As used herein, the term "gene regulatory activity" refers to a polynucleotide molecule capable of affecting transcription or translation of an operably linked polynucleotide molecule. An isolated polynucleotide molecule having gene regulatory activity may provide temporal or spatial expression or modulate levels and rates of expression of the operably linked polynucleotide molecule. An isolated polynucleotide molecule having gene regulatory activity may comprise a promoter, intron, leader, or 3' transcriptional termination region.

As used herein, the term "gene expression" or "expression" refers to the transcription of a DNA molecule into a transcribed RNA molecule. Gene expression may be described as related to temporal, spatial, developmental, or morphological qualities as well as quantitative or qualitative indications. The transcribed RNA molecule may be translated to produce a protein molecule or may provide an antisense or other regulatory RNA molecule.

As used herein, an "expression pattern" is any pattern of differential gene expression. In a preferred embodiment, an expression pattern is selected from the group consisting of tissue, temporal, spatial, developmental, stress, environmental, physiological, pathological, cell cycle, and chemically responsive expression patterns.

As used herein, an "enhanced expression pattern" is any expression pattern for which an operably linked nucleic acid sequence is expressed at a level greater than 0.01%; preferably in a range of about 0.5% to about 20% (w/w) of the total cellular RNA or protein.

As used herein, the term "operably linked" refers to a first polynucleotide molecule, such as a promoter, connected with a second transcribable polynucleotide molecule, such as a gene of interest, where the polynucleotide molecules are so arranged that the first polynucleotide molecule affects the function of the second polynucleotide molecule. The two polynucleotide molecules may or may not be part of a single contiguous polynucleotide molecule and may or may not be adjacent. For example, a promoter is operably linked to a gene of interest if the promoter regulates or mediates transcription of the gene of interest in a cell.

As used herein, the term "transcribable polynucleotide molecule" refers to any polynucleotide molecule capable of being transcribed into a RNA molecule, including but not limited to protein coding sequences (e.g. transgenes) and non-coding sequences (e.g. a molecule useful for gene suppression). Methods are known in the art for constructing and introducing constructs into a cell in such a manner that the transcribable polynucleotide molecule is transcribed into a functional mRNA molecule that is translated and therefore expressed as a protein product. Methods are known in the art for constructing and introducing constructs into a cell in such a manner that the transcribable polynucleotide molecule is transcribed into a molecule that is capable of causing gene suppression. For example, posttranscriptional gene suppression using a construct with an anti-sense oriented transcribable polynucleotide molecule to regulate gene expression in plant cells is disclosed in U.S. Pat. Nos. 5,107,065 and 5,759,829; posttranscriptional gene suppression using a construct with a sense-oriented transcribable polynucleotide molecule to regulate gene expression in plants is disclosed in U.S. Pat. Nos. 5,283,184 and 5,231,020, all of which are hereby incorporated by reference. For the practice of the present invention, conventional compositions and methods for preparing and using constructs and host cells are well known to one skilled in the art, see for example, J F Sambrook, D W Russell, and N Irwin. (2000) Molecular Cloning: A Laboratory Manual, 3rd edition Volumes 1, 2, and 3. Cold Spring Harbor Laboratory Press, hereafter referred to as Sambrook et al., 2000. Constructs may also be constructed to be capable of expressing antisense RNA molecules, in order to inhibit translation of a specific RNA molecule of interest. For the practice of the present invention, conventional compositions and methods for preparing and using constructs and host cells are well known to one skilled in the art, see for example, Molecular Cloning: A Laboratory Manual, 3rd edition Volumes 1, 2, and 3 (2000) J. F. Sambrook, D. W. Russell, and N. Irwin, Cold Spring Harbor Laboratory Press.

Promoters

The present invention describes the composition and utility for eukaryotic translation Initiation Factor non-coding regulatory element molecules from *Nicotiana tabacum*, *Arabidopsis thaliana*, and *Medicago truncatula*, hereinafter referred to as eIF-NCRE molecules. These eIF-NCRE molecules include promoters.

As used herein, the term "promoter" refers to a polynucleotide molecule that is involved in recognition and binding of RNA polymerase II and other proteins such as transcription factors (trans-acting protein factors that regulate transcription) to initiate transcription of an operably linked gene. Promoters may themselves contain sub-elements such as cis-elements or enhancer domains that effect the transcription of operably linked genes. A "plant promoter" is a native or non-native promoter that is functional in plant cells. A plant promoter can be used as a 5' regulatory element for modulating expression of an operably linked gene or genes. Plant promoters may be defined by their temporal, spatial, or developmental expression pattern.

Any of the nucleic acid molecules described herein may comprise nucleic acid sequences comprising promoters. Promoters of the present invention can include between about 300 bp upstream and about 10 kb upstream of the trinucleotide ATG sequence at the start site of a protein coding region. Promoters of the present invention can preferably include between about 300 bp upstream and about 5 kb upstream of the trinucleotide ATG sequence at the start site of a protein coding region. Promoters of the present invention can more preferably include between about 300 bp upstream and about 2 kb upstream of the trinucleotide ATG sequence at the start site of a protein coding region. Promoters of the present invention can include between about 300 bp upstream and about 1 kb upstream of the trinucleotide ATG sequence at the start site of a protein coding region. While in many circumstances a 300 bp promoter may be sufficient for expression, additional sequences may act to further regulate expression, for example, in response to biochemical, developmental or environmental signals.

Promoter Activity

The activity or strength of a promoter may be measured in terms of the amount of mRNA or protein accumulation it specifically produces, relative to the total amount of mRNA or protein. The promoter preferably expresses an operably linked nucleic acid sequence at a level greater than 0.01%, preferably in a range of about 0.5% to about 20% (w/w) of the total cellular RNA or protein.

Alternatively, the activity or strength of a promoter may be expressed relative to a well-characterized promoter (for which transcriptional activity was previously assessed). For example, a less-characterized promoter may be operably linked to a reporter sequence (e.g., GUS) and introduced into a specific cell type. A well-characterized promoter (e.g. the 35S promoter) is similarly prepared and introduced into the same cellular context. Transcriptional activity of the unknown promoter is determined by comparing the amount of reporter expression, relative to the well characterized promoter. In one embodiment, the activity of the present promoter is as strong as the 35S promoter when compared in the same cellular context. The cellular context is preferably maize, sorghum, corn, barley, wheat, canola, soybean, or maize; and more preferably is maize, sorghum, corn, barley, or wheat; and most preferably is maize.

Cis Elements

Promoters of the present invention may contain one or more of the following elements: a CAAT, a GC, or a TATA cis element. Moreover, the promoters of the present invention may contain one or more cis elements in addition to a GC, CAAT and/or a TATA box.

Many regulatory elements act in cis fashion ("cis elements") and are believed to affect DNA topology, producing local conformations that selectively allow or restrict access of RNA polymerase to the DNA template or that facilitate selective opening of the double helix at the site of transcriptional initiation. Cis elements occur within, but are not limited to promoters, and promoter modulating sequences (inducible elements). Cis elements can be identified using known cis elements as a target sequence or target motif in the BLAST programs of the present invention.

Promoters of the present invention may include homologues of cis elements known to effect gene regulation and that show homology with the promoter sequences of the present invention.

5' Non-Translated Leader and Enhancer Sequences

The present invention describes the composition and utility for eukaryotic translation Initiation Factor non-coding regulatory element molecules from *Nicotiana tabacum*, *Arabidopsis thaliana*, and *Medicago truncatula*, hereinafter referred to as eIF-NCRE molecules. These eIF-NCRE molecules include 5' non-translated leader sequences.

As used herein, the term "leader" refers to a non-coding polynucleotide molecule. A leader may be isolated from the untranslated 5' region (5' UTR) of a genomic copy of a gene and defined generally as a segment between the transcription start site (TSS) and the coding sequence start site. Alternately, leaders may be synthetically produced or manipulated non-coding DNA elements. A "plant leader" is a native or non-native leader that is functional in plant cells. A plant leader can be used as a 5' regulatory element for modulating expression of an operably linked gene or genes.

As used herein, the term "enhancer domain" refers to a cis-acting transcriptional regulatory element, a.k.a. cis-element, which confers an aspect of the overall control of gene expression. An enhancer domain may function to bind transcription factors. Some enhancer domains bind more than one transcription factor, and transcription factors may interact with different affinities with more than one enhancer domain. Enhancer domains can be identified by a number of techniques, including deletion analysis, i.e., deleting one or more nucleotides from the 5' end or internal to a promoter; DNA binding protein analysis using DNase I footprinting, methylation interference, electrophoresis mobility-shift assays, in vivo genomic footprinting by ligation-mediated PCR, and other conventional assays; or by DNA sequence similarity analysis with known cis-element motifs by conventional DNA sequence comparison methods. The fine structure of an enhancer domain can be further studied by mutagenesis (or substitution) of one or more nucleotides or by other conventional methods. Enhancer domains can be obtained by chemical synthesis or by isolation from promoters that include such elements, and they can be synthesized with additional flanking nucleotides that contain useful restriction enzyme sites to facilitate subsequence manipulation.

Translational enhancers may also be incorporated as part of the recombinant vector. Thus the recombinant vector may preferably contain one or more 5' non-translated leader sequences which serve to enhance expression of the nucleic acid sequence. Such enhancer sequences may be desirable to increase or alter the translational efficiency of the resultant mRNA. Examples of other non-coding regulatory element 5' nucleic acid leader sequences include dSSU 5', PetHSP70 5', and GmHSP17.9 5'.

Introns

The present invention describes the composition and utility for eukaryotic translation Initiation Factor non-coding regulatory element molecules from *Nicotiana tabacum*, *Arabidopsis thaliana*, and *Medicago truncatula*, hereinafter referred to as eIF-NCRE molecules. These eIF-NCRE molecules include introns.

As used herein, the term "intron" refers to a non-coding polynucleotide molecule. Introns may be isolated from the intervening (non-coding) sequence of a genomic copy of a gene and may be defined generally as a region spliced out during mRNA processing prior to translation. Alternately, introns may be synthetically produced or manipulated non-coding DNA elements. Introns may themselves contain sub-elements such as cis-elements or enhancer domains that effect the transcription of operably linked genes. A "plant intron" is a native or non-native intron that is functional in plant cells. A plant intron can be used as a regulatory element for modulating expression of an operably linked gene or genes.

The transcribable polynucleotide molecule sequence in the recombinant vector may comprise introns. The introns may be heterologous with respect to the transcribable polynucleotide molecule sequence. Examples of other non-coding regulatory element introns include the corn actin intron and the corn HSP70 intron.

Transcribable polynucleotide Molecules

The eIF-NCRE molecules of the present invention may be operably linked to a transcribable polynucleotide molecule sequence that is heterologous with respect to the eIF-NCRE molecules.

The phrase "heterologous" refers to the relationship between two or more nucleic acid or protein sequences that are derived from different sources. For example, a promoter is heterologous with respect to a transcribable polynucleotide sequence if such a combination is not normally found in nature. In addition, a particular sequence may be "heterologous" with respect to a cell or organism into which it is inserted (i.e. does not naturally occur in that particular cell or organism).

The transcribable polynucleotide molecule sequence may generally be any nucleic acid sequence for which an increased level of transcription is desired. The transcribable polynucleotide molecule sequence preferably encodes a polypeptide that is suitable for incorporation into the diet of a human or an animal. Suitable transcribable polynucleotide molecule sequence include but are not limited to those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, and an insecticidal protein.

Alternatively, the eIF-NCRE molecules and transcribable polynucleotide molecule sequence may be designed to downregulate a specific nucleic acid sequence. This is typically accomplished by linking the eIF-NCRE molecules to a transcribable polynucleotide molecule sequence that is oriented in the antisense direction. One of ordinary skill in the art is familiar with such antisense technology. Briefly, as the antisense nucleic acid sequence is transcribed, it hybridizes to and sequesters a complimentary nucleic acid sequence inside the cell. This duplex RNA molecule cannot be translated into a protein by the cell's translational machinery. Any nucleic acid sequence may be negatively regulated in this manner.

Modified Transcribable Polynucleotide Molecule Sequences

The eIF-NCRE molecules of the present invention may also be operably linked to a modified transcribable polynucleotide molecule sequence that is heterologous with respect to the eIF-NCRE molecules. The transcribable polynucleotide molecule sequence may be modified to provide various desirable features. For example, a transcribable polynucleotide molecule sequence may be modified to increase the content of essential amino acids, enhance translation of the amino acid sequence, alter post-translational modifications (e.g., phosphorylation sites), transport a translated product to a compartment inside or outside of the cell, improve protein stability, insert or delete cell signaling motifs, etc.

Polynucleotide Molecule Isolation and Modification Methods

The present invention includes a polynucleotide molecule having a nucleic acid sequence that: i) hybridizes under stringent conditions with a sequence selected from the group consisting of SEQ ID NO: 1 through SEQ ID NO: 11, or any complements thereof, or any fragments thereof; or ii) exhibits an 85% or greater identity to a sequences elected from the group consisting of SEQ ID NO: 1 through SEQ ID NO: 11, any complements thereof, or any fragments thereof. The present invention also provides a nucleic acid molecule comprising a nucleic acid sequences elected from the group consisting of SEQ ID NO:1 through SEQ ID NO:11, any complements thereof, or any fragments thereof.

As used herein, an "isolated polynucleotide molecule" refers to a RNA or DNA molecule that is at least partially separated from other molecules normally associated with it in its native state. In one embodiment, the term "isolated" is also used herein in reference to a polynucleotide molecule that is at least partially separated from nucleic acids which normally flank the polynucleotide in its native state. Thus, polynucleotides fused to regulatory or coding sequences with which they are not normally associated, for example as the result of recombinant techniques, are considered isolated herein. Such molecules are considered isolated even when present, for example in the chromosome of a host cell, or in a nucleic acid solution. The term "isolated" as used herein is not intended to encompass molecules present in their native state. An isolated polynucleotide is an "isolated" molecule if it occurs as a component of a transgene in a transgenic plant. The use of the isolated polynucleotide of the present invention in a transgenic plant is an object of the present invention.

The term "hybridization" refers generally to the ability of nucleic acid molecules to join via complementary base strand pairing. Such hybridization may occur when nucleic acid molecules are contacted under appropriate conditions (see also, "specific hybridization," below).

"Specifically hybridizes" refers to the ability of two nucleic acid molecules to form an anti-parallel, double-stranded nucleic acid structure. A nucleic acid molecule is said to be the "complement" of another nucleic acid molecule if they exhibit "complete complementarity," i.e., each nucleotide in one sequence is complementary to its base pairing partner nucleotide in another sequence. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Nucleic acid molecules that hybridize to other nucleic acid molecules, e.g., at least under low stringency conditions are said to be "hybridizable cognates" of the other nucleic acid molecules. Conventional low stringency and high stringency conditions are described herein and by Sambrook et al., Molecular Cloning, A Laboratory Manual, 2nd Ed., Cold Spring Harbor Press, Cold Spring Harbor, N.Y. (1989) and by Haymes et al., Nucleic Acid Hybridization, A Practical Approach, IRL Press, Washington, D.C. (1985). Departures from complete complementarity are permissible, as long as such departures do not completely preclude the capacity of the molecules to form a double-stranded structure.

As used herein "sequence identity" refers to the extent to which two optimally aligned polynucleotide or peptide sequences are invariant throughout a window of alignment of components, e.g., nucleotides or amino acids. An "identity fraction" for aligned segments of a test sequence and a reference sequence is the number of identical components which are shared by the two aligned sequences divided by the total number of components in reference sequence segment, i.e., the entire reference sequence or a smaller defined part of the reference sequence.

As used herein, the term "percent sequence identity" or "percent identity" refers to the percentage of identical nucleotides in a linear polynucleotide sequence of a reference polynucleotide molecule (or its complementary strand) as compared to a test polynucleotide molecule (or its complementary strand) when the two sequences are optimally aligned (with appropriate nucleotide insertions, deletions, or gaps totaling less than 20 percent of the reference sequence over the window of comparison). Optimal alignment of sequences for aligning a comparison window are well known to those skilled in the art and may be conducted by tools such as the local homology algorithm of Smith and Waterman, the homology alignment algorithm of Needleman and Wunsch, the search for similarity method of Pearson and Lipman, and preferably by computerized implementations of these algorithms such as GAP, BESTFIT, FASTA, and TFASTA available as part of the GCG® Wisconsin Package® (Accelrys Inc., San Diego, Calif.). An "identity fraction" for aligned segments of a test sequence and a reference sequence is the number of identical components which are shared by the two aligned sequences divided by the total number of components in the reference sequence segment, i.e., the entire reference sequence or a smaller defined part of the reference sequence. Percent sequence identity is represented as the identity fraction times 100. The comparison of one or more polynucleotide sequences may be to a full-length polynucleotide sequence or a portion thereof, or to a longer polynucleotide sequence.

As used herein, the term "substantial percent sequence identity" refers to a percent sequence identity of at least about 70% sequence identity, at least about 80% sequence identity, at least about 85% sequence identity, at least about 90% sequence identity, or even greater sequence identity, such as about 95% or about 98% or about 99% sequence identity. Thus, one embodiment of the invention is a polynucleotide molecule that has at least about 70% sequence identity, at least about 80% sequence identity, at least about 85% sequence identity, at least about 90% sequence identity, or even greater sequence identity, such as about 95% or about 98% or about 99% sequence identity with a polynucleotide sequence described herein. Polynucleotide molecules that are capable of regulating or affecting the transcription of an operably linked transcribable polynucleotide molecules and have a substantial percent sequence identity to the polynucleotide sequences of the polynucleotide molecules provided herein are encompassed within the scope of this invention.

"Homology" refers to the level of similarity between two or more nucleic acid or amino acid sequences in terms of percent of positional identity (i.e., sequence similarity or identity). Homology also refers to the concept of similar functional properties among different nucleic acids or proteins.

Any number of methods well known to those skilled in the art can be used to isolate fragments of a polynucleotide molecule disclosed herein. For example, PCR (polymerase chain reaction) technology can be used to amplify flanking regions from a genomic library of a plant using publicly available sequence information. A number of methods are known to those of skill in the art to amplify unknown DNA sequences adjacent to a core region of known sequence. Methods include but are not limited to inverse PCR (IPCR), vectorette PCR, Y-shaped PCR, and genome walking approaches. Polynucleotide molecule fragments can also be obtained by other techniques such as by directly synthesizing the fragment by chemical means, as is commonly practiced by using an automated oligonucleotide synthesizer. For the present invention, the polynucleotide molecules were isolated by designing PCR primers based on available sequence information.

Those of skill in the art are familiar with the standard resource materials that describe specific conditions and procedures for the construction, manipulation, and isolation of macromolecules (e.g., polynucleotide molecules, plasmids, etc.), as well as the generation of recombinant organisms and the screening and isolation of polynucleotide molecules.

Polynucleotide Constructs

Any of the eIF-NCRE molecules and transcribable polynucleotide molecule sequences described above may be provided in a construct. Constructs of the present invention would typically contain a promoter, such as provided in SEQ ID NO: 1 or SEQ ID NO: 11, operably linked to a transcribable polynucleotide molecule.

As used herein, the term "construct" or refers to any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked.

As used herein, the term "vector" or "vector construct" refers to any recombinant polynucleotide construct that may be used for the purpose of transformation, i.e. the introduction of heterologous DNA into a host cell.

In addition, constructs may include, but are not limited to additional polynucleotide molecules from the 3'-untranslated region (3' UTR) of plant genes, e.g. a 3' UTR, such as the PI-II termination region of potato, pea rubisco small subunit 3' UTR or the octopine or nopaline synthase 3'termination regions. In addition, constructs may include but are not limited to additional polynucleotide molecules from the 5'-untranslated region (5' UTR) of plant genes which can play an important role in translation initiation and can also be a genetic component in a plant expression construct, such as provided in SEQ ID NO: 1 through SEQ ID NO: 11, e.g. a leader to enhance transgene expression, such as non-translated 5' leader polynucleotide molecules derived from heat shock protein genes which have been demonstrated to enhance gene expression in plants (see for example, U.S. Pat. Nos. 5,659,122 and 5,362,865, the DNA sequence of which are hereby incorporated by reference). In addition, constructs may include but are not limited to additional polynucleotide molecules such as introns, e.g., the first intron of the actin 1 gene from *Oryza saliva* (U.S. Pat. No. 5,641,876), the IS50L intron from the light sensitive 1 gene of *Solanum tuberosum*, the intron of the heat shock protein 70 gene of *Petunia hybrida* (U.S. Pat. No. 5,659,122), the Hsp70 intron of the Heat shock protein 70 gene of *Zea mays* U.S. Pat. No. 5,593, 874), the DNA sequence of which are hereby incorporated by reference. These additional polynucleotide molecules may be derived from a source that is native or heterologous with respect to the other elements present in the construct.

Means for preparing recombinant constructs are well known in the art. Methods for making recombinant vector constructs particularly suited to plant transformation include, without limitation, those described in U.S. Pat. Nos. 4,971, 908, 4,940,835, 4,769,061 and 4,757,011. These type of vectors have also been reviewed (Rodriguez, et al. Vectors: A Survey of Molecular Cloning Vectors and Their Uses, Butterworths, Boston, 1988; Glick et al., Methods in Plant Molecular Biology and Biotechnology, CRC Press, Boca Raton, Fla., 1993).

Typical constructs useful for expression of nucleic acids in higher plants are well known in the art and include vectors derived from the tumor-inducing (Ti) plasmid of *Agrobacterium tumefaciens* (Rogers, et al., *Meth. In Enzymol*, 153: 253-277, 1987). Other recombinant constructs useful for plant transformation, including the pCaMVCN transfer control vector, have also been described (Fromm et al., *Proc. Natl. Acad. Sci. USA*, 82(17): 5824-5828, 1985).

Promoters in the Recombinant Constructs

The promoter used in the recombinant construct preferably transcribes a heterologous transcribable polynucleotide molecule sequence at a high level in a plant. More preferably, the promoter hybridizes to a nucleic acid sequence selected from the group consisting of SEQ ID NO:1 through SEQ ID NO:11, or any complements thereof; or any fragments thereof. Suitable hybridization conditions include those described above. A nucleic acid sequence of the promoter preferably hybridizes, under low or high stringency conditions, with SEQ ID NO:1 through SEQ ID NO:11, or any complements thereof, or any fragments thereof. The promoter most preferably hybridizes under high stringency conditions to a nucleic acid sequences elected from the group consisting of SEQ ID NO:1 through SEQ ID NO:11, or any complements thereof, or any fragments thereof.

In an alternative embodiment, the promoter comprises a nucleic acid sequence that exhibits 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to a nucleic acid sequences elected from the group consisting of SEQ ID NO:1 through SEQ ID NO:11, or any complements thereof, or any fragments thereof. The promoter most preferably comprises a nucleic acid sequences elected from the group consisting of SEQ ID NO:1 through SEQ ID NO:11, or any complements thereof, or any fragments thereof.

Additional Promoters in the Recombinant Construct

One or more additional promoters may also be provided in the recombinant construct. These promoters may be operably linked to any of the transcribable polynucleotide molecule sequences described above. Alternatively, the promoters may be operably linked to other nucleic acid sequences, such as those encoding transit peptides, selectable marker proteins, or antisense sequences.

As used herein, the term "chimeric" refers to the product of the fusion of portions of two or more different polynucleotide molecules. As used herein, the term "chimeric promoter" refers to a promoter produced through the manipulation of known promoters or other polynucleotide molecules. Such chimeric promoters may combine enhancer domains that can confer or modulate gene expression from one or more promoters or regulatory elements, for example, by fusing a heterologous enhancer domain from a first promoter to a second promoter with its own partial or complete regulatory elements. Thus, the design, construction, and use of chimeric promoters according to the methods disclosed herein for modulating the expression of operably linked polynucleotide sequences are encompassed by the present invention.

Novel chimeric promoters can be designed or engineered by a number of methods. For example, a chimeric promoter may be produced by fusing an enhancer domain from a first promoter to a second promoter. The resultant chimeric promoter may have novel expression properties relative to the first or second promoters. Novel chimeric promoters can be constructed such that the enhancer domain from a first promoter is fused at the 5' end, at the 3' end, or at any position internal to the second promoter. For example, one or more caulimovirus enhancer elements fused to the promoter of the present invention. The location of the enhancer domain fusion relative to the second promoter may cause the resultant chimeric promoter to have novel expression properties relative to a fusion made at a different location. Methods for making chimeric promoters particularly suited to plant transformation include, without limitation, those described in U.S. Pat. No. 6,660,911.

These additional promoters may be selected on the basis of the cell type into which the vector construct will be inserted. Promoters which function in bacteria, yeast, and plants are all well taught in the art. The additional promoters may also be selected on the basis of their regulatory features. Examples of such features include enhancement of transcriptional activity, inducibility, tissue-specificity, and developmental stage-specificity. In plants, promoters that are inducible, of viral or synthetic origin, constitutively active, temporally regulated, and spatially regulated have been described (Poszkowski, et al., *EMBO J.*, 3: 2719, 1989; Odell, et al., *Nature*, 313:810, 1985; Chau et al., *Science*, 244:174-181.1989).

Often-used constitutive promoters include the CaMV 35S promoter, the enhanced CaMV 35S promoter, the Figwort Mosaic Virus (FMV) promoter, the mannopine synthase (mas) promoter, the nopaline synthase (nos) promoter, and the octopine synthase (ocs) promoter.

Useful inducible promoters include promoters induced by salicylic acid or polyacrylic acids induced by application of safeners (substituted benzenesulfonamide herbicides), heat-shock promoters, a nitrate-inducible promoter derived from the spinach nitrite reductase transcribable polynucleotide molecule sequence, hormone-inducible promoters, and light-inducible promoters associated with the small subunit of RuBP carboxylase and LHCP families.

Examples of useful tissue-specific, developmentally-regulated promoters include the β-conglycinin 7Sα promoter, and seed-specific promoters. Plant functional promoters useful for preferential expression in seed plastid include those from plant storage proteins and from proteins involved in fatty acid biosynthesis in oilseeds. Examples of such promoters include the 5' regulatory regions from such transcribable polynucleotide molecule sequences as napin, phaseolin, zein, soybean trypsin inhibitor, ACP, stearoyl-ACP desaturase, and oleosin. Seed-specific regulation is discussed in EP 0 255 378. Another exemplary tissue-specific promoter is the lectin promoter, which is specific for seed tissue.

Particularly preferred additional promoters in the recombinant construct include the nopaline synthase (nos), mannopine synthase (mas), and octopine synthase (ocs) promoters, which are carried on tumor-inducing plasmids of *Agrobacterium tumefaciens*; the cauliflower mosaic virus (CaMV) 19S and 35S promoters; the enhanced CaMV 35S promoter; the Figwort Mosaic Virus (FMV) 35S promoter; the light-inducible promoter from the small subunit of ribulose-1,5-bisphosphate carboxylase (ssRUBISCO); the EIF-4A promoter from tobacco (Mandel, et al., *Plant Mol. Biol,* 29: 995-1004, 1995); corn sucrose synthetase; corn alcohol dehydrogenase 1; corn light harvesting complex; corn heat shock protein; the chitinase promoter from *Arabidopsis*; the LTP (Lipid Transfer Protein) promoters from broccoli; petunia chalcone isomerase; bean glycine rich protein 1; Potato patatin; the ubiquitin promoter from maize; and the actin promoter from corn.

The additional promoter is preferably seed selective, tissue selective, constitutive, or inducible. The promoter is most preferably the nopaline synthase (NOS), octopine synthase (OCS), mannopine synthase (MAS), cauliflower mosaic virus 19S and 35S (CaMV19S, CaMV35S), enhanced CaMV (eCaMV), ribulose 1,5-bisphosphate carboxylase (ss-RUBISCO), figwort mosaic virus (FMV), CaMV derived AS4, tobacco RB7, wheat POX1, tobacco EIF-4, lectin protein (Le1), or corn RC2 promoter.

Other Elements in the Recombinant Construct

The present invention includes the composition and utility for constructs comprising eukaryotic translation Initiation Factor non-coding regulatory element molecules from *Nicotiana tabacum*, *Arabidopsis thaliana*, and *Medicago truncatula*, hereinafter referred to as eIF-NCRE molecules. These constructs may include 5' non-translated leader sequences.

Various cis-acting untranslated 5' and 3' non-coding regulatory element sequences may be included in the recombinant nucleic acid construct. Any such regulatory sequences may be provided in a recombinant construct with other regulatory sequences. Such combinations can be designed or modified to produce desirable regulatory features.

5' non-coding regulatory element sequences typically comprise non-translated leader sequences and/or introns.

A 3' non-translated region typically provides a transcriptional termination signal, and a polyadenylation signal which functions in plants to cause the addition of adenylate nucleotides to the 3' end of the mRNA. These may be obtained from the 3' regions to the nopaline synthase (nos) coding sequence, the soybean 7Sα storage protein coding sequence, the albumin coding sequence, and the pea ssRUBISCO E9 coding sequence. Particularly preferred 3' nucleic acid sequences include nos 3', E9 3', ADR12 3', 7Sα 3', 11S 3', and albumin 3'.

Typically, nucleic acid sequences located a few hundred base pairs downstream of the polyadenylation site serve to terminate transcription. These regions are required for efficient polyadenylation of transcribed mRNA.

The recombinant construct may further comprise a nucleic acid sequence encoding a transit peptide. This peptide may be useful for directing a protein to the extracellular space, a chloroplast, or to some other compartment inside or outside of the cell (see, e.g., European Patent Application Publication Number 0218571).

Transcribable Polynucleotide Molecule Sequences in the Recombinant Nucleic Acid Construct The non-coding regulatory element (NCRE) in the recombinant construct is preferably operably linked to a transcribable polynucleotide molecule sequence. Exemplary transcribable polynucleotide molecule sequences, and modified forms thereof, are described in detail above. The NCRE molecules of the present invention may be operably linked to a transcribable polynucleotide molecule sequence that is heterologous with respect to the NCRE. In one aspect, the transcribable polynucleotide molecule sequence may generally be any nucleic acid sequence for which an increased level of transcription is desired. The transcribable polynucleotide molecule sequence preferably encodes a polypeptide that is suitable for incorporation into the diet of a human or an animal. Suitable transcribable polynucleotide molecule sequences include those encoding a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, and an insecticidal protein.

Alternatively, the NCRE or the transcribable polynucleotide molecule sequences may be designed to down-regulate a specific nucleic acid sequence. This is typically accomplished by linking the NCRE to a transcribable polynucleotide molecule sequence that is oriented in the antisense direction. One of ordinary skill in the art is familiar with such antisense technology. Using such an approach, a cellular nucleic acid sequence is effectively down regulated as the subsequent steps of translation are disrupted. Nucleic acid sequences may be negatively regulated in this manner.

Thus, one embodiment of the invention is a polynucleotide molecule such as provided in SEQ ID NO:1 through SEQ ID NO: 11 that is operably linked to a transcribable polynucleotide molecule so as to direct transcription of the transcribable polynucleotide molecule at a desired level or in a desired tissue or developmental pattern upon introduction of the construct into a plant cell. In some cases, the transcribable polynucleotide molecule comprises a protein-coding region of a gene, and a non-coding regulatory element of SEQ ID NO:1 through SEQ ID NO: 11 provides for transcription of a functional mRNA molecule that is translated and expressed as a protein product. Constructs may also be constructed for transcription of antisense RNA molecules or other similar inhibitory RNA molecules in order to suppress expression of a specific gene of interest in a target host cell.

Exemplary transcribable polynucleotide molecules for incorporation into constructs of the present invention include, for example, DNA molecules or genes from a species other than the target gene species, or even genes that originate with or are present in the same species, but are incorporated into recipient cells by genetic engineering methods rather than classical reproduction or breeding techniques. Exogenous gene or genetic element is intended to refer to any gene or polynucleotide molecule that is introduced into a recipient cell. The type of polynucleotide molecule included in the exogenous DNA can include DNA that is already present in the plant cell, DNA from another plant, DNA from a different organism, or a DNA generated externally, such as a DNA molecule containing an antisense message of a gene, or a DNA molecule encoding an artificial or modified version of a gene.

Fusion Proteins

Any of the above described structural nucleic acid sequences, and modified forms thereof, may be linked with additional nucleic acid sequences to encode fusion proteins. The additional nucleic acid sequence preferably encodes at least 1 amino acid, peptide, or protein. Production of fusion proteins is routine in the art and many possible fusion combinations exist.

For instance, the fusion protein may provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids.

Alternatively, the fusion may provide regulatory, enzymatic, cell signaling, or intercellular transport functions. For example, a sequence encoding a chloroplast transit peptide may be added to direct a fusion protein to the chloroplasts within a plant cell. Such fusion partners preferably encode between 1 and 1000 additional amino acids, more preferably between 5 and 500 additional amino acids, and even more preferably between 10 and 250 amino acids.

Where plastid targeting is necessary, for example, the EPSPS enzyme functions in a plant chloroplast, therefore, DNA molecules encoding a chloroplast transit peptide (CTP) are engineered into a DNA molecule encoding an EPSPS protein to encode a fusion protein of the CTP to the N terminus of an EPSPS creating a chimeric molecule. A chimeric polynucleic acid coding sequence is comprised of two or more open reading frames joined in-frame that encode a chimeric protein, for example, a chloroplast transit peptide and an EPSPS enzyme. A chimeric gene refers to the multiple genetic elements derived from heterologous sources operably linked to comprise a gene. In the present invention the DNA construct expresses a chimeric CTP-EPSPS protein that directs the glyphosate resistant EPSPS protein into the plant chloroplast. In a native plant EPSPS gene, chloroplast transit peptide regions are contained in the native coding sequence (for example, CTP2, Klee et al., Mol. Gen. Genet. 210:47-442, 1987). The CTP is cleaved from the EPSPS enzyme at the chloroplast membrane to create a "mature EPSPS or EPSPS enzyme" that refers to the polypeptide sequence of the processed protein product remaining after the chloroplast transit peptide has been removed. The production of glyphosate tolerant plants by expression of a fusion protein comprising an amino-terminal CTP with a glyphosate resistant EPSPS enzyme is well known by those skilled in the art, (U.S. Pat. Nos. 5,627,061, 5,633,435, 5,312,910, EP 0218571, EP 189707, EP 508909, and EP 924299). Those skilled in the art will recognize that various chimeric constructs can be made that utilize the functionality of a particular CTP to import glyphosate resistant EPSPS enzymes into the plant cell chloroplast. The present invention illustrates the utility of the combination of an eIF-NCRE molecule operably linked to a DNA molecule that encodes for a chloroplast transit peptide fused to an EPSP synthase.

NCRE Molecules and Genes of Agronomic Interest

The recombinant construct may also contain one or more additional transcribable polynucleotide molecule sequences. These additional transcribable polynucleotide molecule sequences may generally be any sequences suitable for use in a recombinant construct. Such transcribable polynucleotide molecule sequences include any of the transcribable polynucleotide molecule sequences, and modified forms thereof, described above. The additional transcribable polynucleotide molecule sequences may also be operably linked to any of the above described NCRE sequences. The one or more transcribable polynucleotide molecule sequences may each be operably linked to separate NCRE sequences. Alternatively, the transcribable polynucleotide molecule sequences may be operably linked to a single NCRE (i.e. a single operon).

As used herein, the term "gene of agronomic interest" refers to a transcribable polynucleotide molecule that includes but is not limited to a gene that provides a desirable characteristic associated with plant morphology, physiology, growth and development, yield, nutritional enhancement, disease or pest resistance, or environmental or chemical tolerance.

The additional transcribable polynucleotide molecule sequences preferably encode a gene of agronomic interest, such as but not limited to: a yield protein, a stress resistance protein, a developmental control protein, a tissue differentiation protein, a meristem protein, an environmentally responsive protein, a senescence protein, a hormone responsive protein, an abscission protein, a source protein, a sink protein, a flower control protein, a seed protein, an herbicide resistance protein, a disease resistance protein, a fatty acid biosynthetic enzyme, a tocopherol biosynthetic enzyme, an amino acid biosynthetic enzyme, and an insecticidal protein.

Alternatively, the additional transcribable polynucleotide molecule sequences may be designed to down-regulate a specific nucleic acid sequence. This is typically accomplished by operably linking the second structural amino acid, in an antisense orientation, with a promoter. One of ordinary skill in the art is familiar with such antisense technology. The process is also briefly described above. Any nucleic acid sequence may be negatively regulated in this manner.

In one embodiment of the invention, a polynucleotide molecule as shown in SEQ ID NO: 1 through SEQ ID NO: 11, or any complements thereof or any fragments thereof comprising regulatory elements, such as a promoter, leader, or an intron element, is incorporated into a construct such that a polynucleotide molecule of the present invention is operably linked to a transcribable polynucleotide molecule that is a gene of agronomic interest.

The expression of a gene of agronomic interest is desirable in order to confer an agronomically important trait. A gene of agronomic interest that provides a beneficial agronomic trait to crop plants may be, for example, including, but not limited to genetic elements comprising herbicide resistance (U.S. Pat. Nos. 5,633,435 and 5,463,175), increased yield (U.S. Pat. No. 5,716,837), insect control (U.S. Pat. Nos. 6,063,597; 6,063,756; 6,093,695; 5,942,664; and 6,110,464), fungal disease resistance (U.S. Pat. Nos. 5,516,671; 5,773,696; 6,121, 436; 6,316,407, and U.S. Pat. No. 6,506,962), virus resistance (U.S. Pat. Nos. 5,304,730 and 6,013,864), nematode resistance (U.S. Pat. No. 6,228,992), bacterial disease resistance (U.S. Pat. No. 5,516,671), starch production (U.S. Pat. Nos. 5,750,876 and 6,476,295), modified oils production (U.S. Pat. No. 6,444,876), high oil production (U.S. Pat. Nos. 5,608,149 and 6,476,295), modified fatty acid content (U.S. Pat. No. 6,537,750), high protein production (U.S. Pat. No. 6,380,466), fruit ripening (U.S. Pat. No. 5,512,466), enhanced animal and human nutrition (U.S. Pat. Nos. 5,985, 605 and 6,171,640), biopolymers (U.S. Pat. No. 5,958,745 and U.S. Patent Publication No. US20030028917), environmental stress resistance (U.S. Pat. No. 6,072,103), pharmaceutical peptides (U.S. Pat. No. 6,080,560), improved processing traits (U.S. Pat. No. 6,476,295), improved digestibility (U.S. Pat. No. 6,531,648) low raffinose (U.S. Pat. No. 6,166,292), industrial enzyme production (U.S. Pat. No. 5,543,576), improved flavor (U.S. Pat. No. 6,011,199), nitrogen fixation (U.S. Pat. No. 5,229,114), hybrid seed production (U.S. Pat. No. 5,689,041), and biofuel production (U.S. Pat. No. 5,998,700), the genetic elements, methods, and transgenes described in the patents listed above are hereby incorporated by reference.

Alternatively, a transcribable polynucleotide molecule can effect the above mentioned phenotypes by encoding a RNA molecule that causes the targeted suppression of expression of an endogenous gene, for example via antisense, dsRNA, or cosuppression-mediated mechanisms. The RNA could also be a catalytic RNA molecule (i.e., a ribozyme) engineered to cleave a desired endogenous mRNA product. Thus, any polynucleotide molecule that encodes a protein or mRNA that expresses a phenotype or morphology change of interest may be useful for the practice of the present invention.

The constructs of the present invention are generally double Ti plasmid border DNA constructs that have the right border (RB or AGRtu.RB) and left border (LB or AGRtu.LB) regions of the Ti plasmid isolated from *Agrobacterium tumefaciens* comprising a T-DNA, that along with transfer molecules provided by the *Agrobacterium* cells, permits the integration of the T-DNA into the genome of a plant cell. The constructs also contain the plasmid backbone DNA segments that provide replication function and antibiotic selection in bacterial cells, for example, an *E. coli* origin of replication such as ori322, a broad host range origin of replication such as oriV, rop, or oriRi, and a coding region for a selectable marker such as Spec/Strp that encodes for Tn7 aminoglycoside adenyltransferase (aadA) conferring resistance to spectinomycin or streptomycin, or a gentamicin (Gm, Gent) selectable marker gene. For plant transformation, the host bacterial strain is often *Agrobacterium tumefaciens* ABI, C58, or LBA4404, however, other strains known to those skilled in the art of plant transformation can function in the present invention.

Selectable Markers

The polynucleotide molecules of the present invention can be incorporated into a DNA construct using marker genes as described and tested in transient analyses that provide an indication of gene expression in stable plant systems.

As used herein the term "marker gene" or "selectable marker" refers to any transcribable polynucleotide molecule whose expression can be screened for or scored in some way. Included within the term "selectable markers" is also genes which encode a secretable marker whose secretion can be detected as a means of identifying or selecting for transformed cells.

Methods of testing for marker gene expression in transient assays are known to those of skill in the art. Transient expression of marker genes has been reported using a variety of plants, tissues, and DNA delivery systems. For example, types of transient analyses can include, but are not limited to direct gene delivery via electroporation or particle bombardment of tissues in any transient plant assay using any plant species of interest. Such transient systems would include, but are not limited to electroporation of protoplasts from a variety of tissue sources or particle bombardment of specific tissues of interest. The present invention encompasses the use of any transient expression system to evaluate polynucleotide molecule operably linked to any transcribable polynucleotide molecules, including, but not limited to selected reporter genes, marker genes, or genes of agronomic interest. Examples of plant tissues envisioned to test in transients via an appropriate delivery system would include, but are not limited to leaf base tissues, callus, cotyledons, roots, endosperm, embryos, floral tissue, pollen, and epidermal tissue.

The recombinant construct may further comprise a selectable marker. The nucleic acid sequence serving as the selectable marker functions to produce a phenotype in cells which facilitates their identification relative to cells not containing the marker.

Examples of selectable markers include, but are not limited to, a neo gene, which codes for kanamycin resistance and can be selected for using kanamycin, G418, etc.; a bar gene which codes for bialaphos resistance; a mutant EPSP synthase gene which encodes glyphosate resistance; a nitrilase gene which confers resistance to bromoxynil; a mutant acetolactate synthase gene (ALS) which confers imidazolinone or sulphonylurea resistance (European Patent Application No. 0154204); green fluorescent protein (GFP); and a methotrexate resistant DHFR gene.

Other exemplary selectable markers include: a β-glucuronidase or uidA gene (GUS), which encodes an enzyme for which various chromogenic substrates are known; an R-locus gene, which encodes a product that regulates the production of anthocyanin pigments in plant tissues (; a β-lactamase gene, which encodes an enzyme for which various chromogenic substrates are known (e.g., PADAC, a chromogenic cephalosporin); a luciferase gene; a xylE gene which encodes a catechol dioxygenase that can convert chromogenic catechols; an α-amylase gene; a tyrosinase gene, which encodes an enzyme capable of oxidizing tyrosine to DOPA and dopaquinone (which in turn condenses to melanin); and an α-galactosidase, which will turn a chromogenic α-galactose substrate.

Included within the term "selectable markers" are also genes which encode a secretable marker whose secretion can be detected as a means of identifying or selecting for transformed cells. Examples include markers that encode a secretable antigen that can be identified by antibody interaction, or even secretable enzymes which can be detected catalytically. Selectable secreted marker proteins fall into a number of classes, including small, diffusible proteins which are detectable, (e.g., by ELISA), small active enzymes which are detectable in extracellular solution (e.g., α-amylase, β-lactamase, phosphinothricin transferase), or proteins which are inserted or trapped in the cell wall (such as proteins which include a leader sequences such as that found in the expression unit of extension or tobacco PR-S). Other possible selectable marker genes will be apparent to those of skill in the art.

The selectable marker is preferably GUS, green fluorescent protein (GFP), neomycin phosphotransferase II (nptII), luciferase (LUX), an antibiotic resistance coding sequence, or an herbicide (e.g., glyphosate) resistance coding sequence. The selectable marker is most preferably a kanamycin, hygromycin, or herbicide resistance marker.

Any scorable or screenable marker gene can be used in a transient assay. Exemplary marker genes for transient analyses of the promoters or promoter fragments of the present invention include a GUS gene (U.S. Pat. No. 5,599,670, hereby incorporated by reference) or a GFP gene (U.S. Pat. No. 5,491,084, hereby incorporated by reference). The constructs containing the polynucleotide molecule operably linked to a marker gene are delivered to the tissues and the tissues are analyzed by the appropriate mechanism, depending on the marker. The quantitative or qualitative analyses are used as a tool to evaluate the potential expression profile of the polynucleotide molecule when operably linked to genes of agronomic interest in stable plants.

Thus, in one preferred embodiment, a polynucleotide molecule of the present invention, such as shown in SEQ ID NO:1 through SEQ ID NO: 11, is incorporated into a DNA construct such that a polynucleotide molecule of the present invention is operably linked to a transcribable polynucleotide molecule that provides for a selectable, screenable, or scorable marker. Markers for use in the practice of the present invention include, but are not limited to transcribable polynucleotide molecules encoding β-glucuronidase (GUS), green fluorescent protein (GFP), luciferase (LUC), proteins that confer antibiotic resistance, or proteins that confer herbicide tolerance. Useful antibiotic resistance markers, including those encoding proteins conferring resistance to kanamycin (nptII), hygromycin B (aph IV), streptomycin or spectinomycin (aad, spec/strep) and gentamycin (aac3 and aacC4) are known in the art.

Herbicides for which transgenic plant tolerance has been demonstrated and the method of the present invention can be applied, include but are not limited to: glyphosate, glufosinate, sulfonylureas, imidazolinones, bromoxynil, delapon, cyclohezanedione, protoporphyrionogen oxidase inhibitors, and isoxasflutole herbicides.

"Glyphosate" refers to N-phosphonomethylglycine and its salts, Glyphosate is the active ingredient of Roundup® herbicide (Monsanto Co.). Plant treatments with "glyphosate" refer to treatments with the Roundup® or Roundup Ultra® herbicide formulation, unless otherwise stated. Glyphosate as N-phosphonomethylglycine and its salts (not formulated Roundup® herbicide) are components of synthetic culture media used for the selection of bacteria and plant tolerance to glyphosate or used to determine enzyme resistance in in vitro biochemical assays. Examples of commercial formulations of glyphosate include, without restriction, those sold by Monsanto Company as ROUNDUP®, ROUNDUP® ULTRA, ROUNDUP® ULTRAMAX, ROUNDUP®, ROUNDUP® CT, ROUNDUP® EXTRA, ROUNDUP® BIACTIVE, ROUNDUP® BIOFORCE, RODEO®, POLARIS®, SPARK® and ACCORD® herbicides, all of which contain glyphosate as its isopropylammonium salt; WEATHER-MAX®, which contains glyphosate as its potassium salt; those sold by Monsanto Company as ROUNDUP® DRY and RIVAL® herbicides, which contain glyphosate as its ammonium salt; that sold by Monsanto Company as ROUNDUP® GEOFORCE, which contains glyphosate as its sodium salt; and that sold by Zeneca Limited as TOUCHDOWN® herbicide, which contains glyphosate as its trimethylsulfonium salt.

Polynucleotide molecules encoding proteins involved in herbicide tolerance are known in the art, and include, but are not limited to a polynucleotide molecule encoding 5-enolpyruvylshikimate-3-phosphate synthase (EPSPS) described in U.S. Pat. Nos. 5,627,061, 5,633,435, 6,040,497 and in 5,094,945 for glyphosate tolerance, all of which are hereby incorporated by reference; polynucleotides encoding a glyphosate oxidoreductase and a glyphosate-N-acetyl transferase (GOX, U.S. Pat. No. 5,463,175 and GAT, U.S. Patent publication 20030083480, herein incorporated by reference); a polynucleotide molecule encoding bromoxynil nitrilase (Bxn) described in U.S. Pat. No. 4,810,648 for Bromoxynil tolerance, which is hereby incorporated by reference; a polynucleotide molecule encoding phytoene desaturase (crtI) described in Misawa et al, (1993) *Plant J.* 4:833-840 and Misawa et al, (1994) *Plant J.* 6:481-489 for norflurazon tolerance; a polynucleotide molecule encoding acetohydroxyacid synthase (AHAS, aka ALS) described in Sathasiivan et al. (1990) *Nucl. Acids Res.* 18:2188-2193 for tolerance to sulfonylurea herbicides; and the bar gene described in DeBlock, et al. (1987) *EMBO J.* 6:2513-2519 for glufosinate and bialaphos tolerance; resistant hydroxyphenyl pyruvate dehydrogenase (HPPD, U.S. Pat. No. 6,768,044). The promoter of the present invention can express genes that encode for phosphinothricin acetyltransferase, glyphosate resistant EPSPS, aminoglycoside phosphotransferase, hydroxyphenyl pyruvate dehydrogenase, hygromycin phosphotransferase, neomycin phosphotransferase, dalapon dehalogenase, bromoxynil resistant nitrilase, anthranilate synthase, glyphosate oxidoreductase and glyphosate-N-acetyl transferase.

Transformed Plants and Plant Cells

The invention is also directed to a method of producing transformed cells which comprise, in a 5' to 3' orientation, one or more non-coding regulatory elements operably linked to a heterologous transcribable polynucleotide molecule sequence. Other sequences may also be introduced into the cell along with the non-coding regulatory elements and transcribable polynucleotide molecule sequence. These other sequences may include 3' transcriptional terminators, 3' polyadenylation signals, other untranslated sequences, transit or targeting sequences, selectable markers, enhancers, and operators.

The method of transformation generally comprises the steps of selecting a suitable host cell, transforming the host cell with a recombinant vector, and obtaining the transformed host cell.

As used herein, the term "transformed" refers to a cell, tissue, organ, or organism into which has been introduced a foreign polynucleotide molecule, such as a construct. The introduced polynucleotide molecule may be integrated into the genomic DNA of the recipient cell, tissue, organ, or organism such that the introduced polynucleotide molecule is inherited by subsequent progeny. A "transgenic" or "transformed" cell or organism also includes progeny of the cell or organism and progeny produced from a breeding program employing such a transgenic plant as a parent in a cross and exhibiting an altered phenotype resulting from the presence of a foreign polynucleotide molecule.

Preferred recombinant constructs, transcribable polynucleotide molecule sequences, non-coding regulatory elements, and other regulatory elements are described above. The non-coding regulatory element preferably has a nucleic acid sequence that hybridizes under stringent conditions with SEQ ID NO:1 through SEQ ID NO:11, or any complement thereof; or exhibits 85% or greater identity, and more preferably at least 86 or greater, 87 or greater, 88 or greater, 89 or greater, 90 or greater, 91 or greater, 92 or greater, 93 or greater, 94 or greater, 95 or greater, 96 or greater, 97 or greater, 98 or greater, or 99% or greater identity to SEQ ID NO:1 through SEQ ID NO:11. The recombinant construct used to transform the host cell typically comprises, in a 5' to 3' orientation: a promoter to direct the transcription of a transcribable polynucleotide molecule sequence, a transcribable polynucleotide molecule sequence, a 3' transcriptional terminator, and a 3' polyadenylation signal. The recombinant vector may further comprise untranslated nucleic acid sequences, transit and targeting nucleic acid sequences, selectable markers, enhancers, or operators. Suitable recombinant vectors, transcribable polynucleotide molecule sequences, promoters, and other regulatory elements include, without limitation, those described above.

Technology for introduction of DNA into cells is well known to those of skill in the art. These methods can generally be classified into five categories: (1) chemical methods (Graham and Van der Eb, *Virology*, 54(2): 536-539, 1973; Zatloukal, et al., *Ann. N.Y. Acad. Sci.*, 660: 136-153, 1992); (2) physical methods such as microinjection (Capecchi, *Cell*, 22(2): 479-488, 1980), electroporation (Wong and Neumann, *Biochim. Biophys. Res. Commun.*, 107(2): 584-587, 1982; Fromm et al., *Proc. Natl. Acad. Sci. USA*, 82(17): 5824-5828, 1985; U.S. Pat. No. 5,384,253) and particle acceleration (Johnston and Tang, *Methods Cell Biol.*, 43(A): 353-365, 1994; Fynan et al., *Proc. Natl. Acad. Sci. USA*, 90(24): 11478-11482, 1993); (3) viral vectors (Clapp, *Clin. Perinatol.*, 20(1): 155-168, 1993; Lu, et al., *J. Exp. Med.*, 178(6): 2089-2096, 1993; Eglitis and Anderson, *Biotechniques*, 6(7): 608-614, 1988); (4) receptor-mediated mechanisms (Curiel et al., *Hum. Gen. Ther.*, 3(2):147-154, 1992; Wagner, et al., *Proc. Natl. Acad. Sci. USA*, 89(13): 6099-6103, 1992), and (5) bacterial mediated mechanisms such as with *Agrobacterium*. Alternatively, nucleic acids can be directly introduced into pollen by directly injecting a plant's reproductive organs (Zhou, et al., *Methods in Enzymology*, 101: 433, 1983; Hess, *Intern Rev. Cytol.*, 107: 367, 1987; Luo, et al., *Plant Mol. Biol. Reporter*, 6: 165, 1988; Pena, et al., *Nature*, 325: 274, 1987). Other transformation methods include, for example, protoplast transformation as illustrated in U.S. Pat. No. 5,508,184. The nucleic acids may also be injected into immature embryos (Neuhaus, et al., *Theor. Appl. Genet.*, 75: 30, 1987).

The most commonly used methods for transformation of plant cells are the *Agrobacterium*-mediated DNA transfer process (Fraley et al., Proc. Natl. Acad. Sci. U.S.A., 80: 4803, 1983) (as illustrated in U.S. Pat. Nos. 5,824,877; 5,591,616; 5,981,840; and 6,384,301) and the biolistics or microprojectile bombardment mediated process (i.e. the gene gun) (such as described in U.S. Pat. Nos. 5,015,580; 5,550,318; 5,538,880; 6,160,208; 6,399,861; and 6,403,865). Typically, nuclear transformation is desired but where it is desirable to specifically transform plastids, such as chloroplasts or amyloplasts, plant plastids may be transformed utilizing a microprojectile mediated delivery of the desired polynucleotide for certain plant species such as tobacco, *Arabidopsis*, potato and *Brassica* species.

*Agrobacterium*-mediated transformation is achieved through the use of a genetically engineered soil bacterium belonging to the genus *Agrobacterium*. Several *Agrobacterium* species mediate the transfer of a specific DNA known as "T-DNA", that can be genetically engineered to carry any desired piece of DNA into many plant species. The major events marking the process of T-DNA mediated pathogenesis are: induction of virulence genes, processing and transfer of T-DNA. This process is the subject of many reviews (Ream, Ann. Rev. Phytopathol. 27: 583-618, 1989; Howard and Citovsky, Bioassays, 12:103-108, 1990; Kado, Crit. Rev. Plant Sci. 10:1-32, 1991; Zambryski, Annual Rev. Plant Physiol. Plant Mol. Biol., 43: 465-490, 1992; Gelvin, In Transgenic Plants, Kung and Wu eds., Academic Press, San Diego, pp. 49-87, 1993; Binns and Howitz, 1994, In Bacterial Pathogenesis of Plants and Animals (Dang, ed.). Berlin: Springer Verlag, pp. 119-138, 1994; Hooykaas and Beijersbergen, Ann. Rev. Phytopathol. 32:157-179, 1994; Lessl and Lanka, Cell 77:321-324, 1994; Zupan and Zambryski, Annual Rev. Phytopathol. 27, 583-618, 1995).

With respect to microprojectile bombardment (U.S. Pat. Nos. 5,550,318; 5,538,880; 5,610,042; and PCT Publication WO 95/06128; each of which is specifically incorporated herein by reference in its entirety), particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the microprojectile stopping plate.

Microprojectile bombardment techniques are widely applicable, and may be used to transform virtually any plant species. Examples of species that have been transformed by microprojectile bombardment include monocot species such as maize (PCT Publication WO 95/06128), barley (Ritala et al., 1994; Hensgens et al., 1993), wheat (U.S. Pat. No. 5,563,055, specifically incorporated herein by reference in its entirety), rice (Hensgens et al., 1993), oat (Torbet et al., 1995; Torbet et al., 1998), rye (Hensgens et al., 1993), sugarcane (Bower et al., 1992), and sorghum (Casa et al., 1993; Hagio et al., 1991); as well as a number of dicots including tobacco (Tomes et al., 1990; Buising and Benbow, 1994), soybean (U.S. Pat. No. 5,322,783, specifically incorporated herein by reference in its entirety), sunflower (Knittel et al. 1994), peanut (Singsit et al., 1997), cotton (McCabe and Martinell, 1993), tomato (Van Eck et al. 1995), and legumes in general (U.S. Pat. No. 5,563,055, specifically incorporated herein by reference in its entirety).

To select or score for transformed plant cells regardless of transformation methodology, the DNA introduced into the cell contains a gene that functions in a regenerable plant tissue to produce a compound that confers upon the plant tissue resistance to an otherwise toxic compound. Genes of interest for use as a selectable, screenable, or scorable marker will include but are not limited to GUS, green fluorescent protein (GFP), luciferase (LUX), antibiotic or herbicide tolerance genes. Examples of antibiotic resistance genes include the penicillins, kanamycin (and neomycin, G418, bleomycin); methotrexate (and trimethoprim); chloramphenicol; kanamycin and tetracycline.

Particularly preferred selectable marker genes for use in the present invention will include genes that confer resistance to compounds such as antibiotics like kanamycin (nptII), hygromycin B (aph IV) and gentamycin (aac3 and aacC4) (Dekeyser et al., Plant Physiol., 90:217-223, 1989), and herbicides like glyphosate (Della-Cioppa et al., Bio/Technology, 5:579-584, 1987). Other selection devices can also be implemented including but not limited to tolerance to phosphinothricin, bialaphos, and positive selection mechanisms (Joersbo et al., Mol. Breed., 4:111-117, 1998) and are considered within the scope of the present invention.

The transformed cells, identified by selection or screening and cultured in an appropriate medium that supports regeneration, will then be allowed to mature into plants.

The present invention can be used with any transformable cell or tissue. By transformable as used herein is meant a cell or tissue that is capable of further propagation to give rise to a plant. Those of skill in the art recognize that a number of plant cells or tissues are transformable in which after insertion of exogenous DNA and appropriate culture conditions the plant cells or tissues can form into a differentiated plant. Tissue suitable for these purposes can include but is not limited to immature embryos, scutellar tissue, suspension cell cultures, immature inflorescence, shoot meristem, nodal explants, callus tissue, hypocotyl tissue, cotyledons, roots, and leaves.

The regeneration, development, and cultivation of plants from transformed plant protoplast or explants is well taught in the art (Weissbach and Weissbach, *Methods for Plant Molecular Biology*, (Eds.), Academic Press, Inc., San Diego, Calif., 1988; Horsch et al., *Science,* 227: 1229-1231, 1985). This regeneration and growth process typically includes the steps of selecting transformed cells and culturing those individualized cells through the usual stages of embryonic development through the rooted plantlet stage. Transgenic embryos and seeds are similarly regenerated. In this method, transformants are generally cultured in the presence of a selective media which selects for the successfully transformed cells and induces the regeneration of plant shoots (Fraley et al., *Proc. Natl. Acad. Sci. U.S.A.,* 80: 4803, 1983). These shoots are typically obtained within two to four months. The resulting transgenic rooted shoots are thereafter planted in an appropriate plant growth medium such as soil. Cells that survive the exposure to the selective agent, or cells that have been scored positive in a screening assay, may be cultured in media that supports regeneration of plants. The shoots are then transferred to an appropriate root-inducing medium containing the selective agent and an antibiotic to prevent bacterial growth. Many of the shoots will develop roots. These are then transplanted to soil or other media to allow the continued development of roots. The method, as outlined, will generally vary depending on the particular plant strain employed.

The regenerated transgenic plants are self-pollinated to provide homozygous transgenic plants. Alternatively, pollen obtained from the regenerated transgenic plants may be crossed with non-transgenic plants, preferably inbred lines of agronomically important species. Conversely, pollen from non-transgenic plants may be used to pollinate the regenerated transgenic plants.

The transgenic plant may pass along the transformed nucleic acid sequence to its progeny. The transgenic plant is preferably homozygous for the transformed nucleic acid sequence and transmits that sequence to all of its offspring upon as a result of sexual reproduction. Progeny may be grown from seeds produced by the transgenic plant. These additional plants may then be self-pollinated to generate a true breeding line of plants.

The progeny from these plants are evaluated, among other things, for gene expression. The gene expression may be detected by several common methods such as western blotting, northern blotting, immunoprecipitation, and ELISA. The transformed plants are also analyzed for the presence of the genes of interest and the expression level and/or profile conferred by the non-coding regulatory elements of the present invention. Those of skill in the art are aware of the numerous methods available for the analysis of transformed plants. For example, methods for plant analysis include, but are not limited to Southern blots or northern blots, PCR-based approaches, biochemical analyses, phenotypic screening methods, field evaluations, and immunodiagnostic assays.

Methods for specifically transforming dicots are well known to those skilled in the art. Transformation and plant regeneration using these methods have been described for a number of crops including, but not limited to, cotton (*Gossypium hirsutum*), soybean (*Glycine max*), peanut (*Arachis hypogaea*), and members of the genus *Brassica*. Methods for transforming dicots, primarily by use of *Agrobacterium tumefaciens* and obtaining transgenic plants have been published for cotton (U.S. Pat. Nos. 5,004,863; 5,159,135; 5,518, 908); soybean (U.S. Pat. Nos. 5,569,834; 5,416,011; McCabe, et al., *Biotechnology*, 6: 923, 1988; Christou et al., *Plant Physiol.* 87:671-674 (1988)); *Brassica* (U.S. Pat. No. 5,463,174); peanut (Cheng et al., *Plant Cell Rep.* 15:653-657 (1996), McKently et al., *Plant Cell Rep.* 14:699-703 (1995)); papaya; and pea (Grant et al., *Plant Cell Rep.* 15:254-258 (1995)).

Methods for transforming monocots are well known to those skilled in the art. Transformation and plant regeneration using these methods have been described for a number of crops including, but not limited to, barley (*Hordeum vulgarae*); maize (*Zea mays*); oats (*Avena sativa*); orchard grass (*Dactylis glomerata*); rice (Oryza saliva, including indica and japonica varieties); sorghum (*Sorghum bicolor*); sugar cane (*Saccharum* sp); tall fescue (*Festuca arundinacea*); turfgrass species (e.g. species: *Agrostis stolonifera, Poa pratensis, Stenotaphrum secundatum*); wheat (*Triticum aestivum*), and alfalfa (*Medicago saliva*). It is apparent to those of skill in the art that a number of transformation methodologies can be used and modified for production of stable transgenic plants from any number of target crops of interest.

It is apparent to those of skill in the art that a number of transformation methodologies can be used and modified for production of stable transgenic plants from any number of target crops of interest.

Transgenic Plants and Transgenic Seeds

The seeds of this invention can be harvested from fertile transgenic plants and be used to grow progeny generations of transformed plants of this invention including hybrid plant lines comprising the construct of this invention and expressing a gene of agronomic interest.

The present invention also provides for parts of the plants of the present invention. Plant parts, without limitation, include seed, endosperm, ovule and pollen. In a particularly preferred embodiment of the present invention, the plant part is a seed.

Utilization of Transgenic Plants

Still yet another aspect of the invention is a method of inhibiting weed growth in a field of transgenic crop plants comprising: (i) planting transgenic plants transformed with an expression cassette comprising (a) a eukaryotic translation initiation factor non-coding regulatory element polynucleotide molecule active in the plant and operably linked to a DNA molecule encoding a glyphosate resistant EPSPS and (ii) applying glyphosate to the field at an application rate that inhibits the growth of weeds, wherein the growth and yield of the transgenic crop plant is not substantially affected by the glyphosate application. In particular embodiments, the promoter is SEQ ID NO:1 or SEQ ID NO:2. The glyphosate application rate is the effective rate necessary to control weeds in a particular glyphosate tolerant crop, these rates may range from 8 oz/A to 256 oz/A, preferably 16 oz/A to 128 oz/A, more preferably 32 oz/A to 96 oz/A. The glyphosate is applied at least once during the growth of the glyphosate tolerant crop and may be applied 2, 3 or 4 times during the growth of the crop or more as necessary to control weeds in the field. In particular embodiments, the transgenic plants are capable of tolerating an application rate up to 256 ounces/acre. In particular embodiments, the transgenic plants are capable of tolerating an application rate ranging from 8 ounces/acre to 128 ounces/acre. In particular embodiments, the transgenic plants are capable of tolerating an application rate ranging from 32 ounces/acre to 96 ounces/acre.

Other Transformed Organisms

Any of the above described promoters and transcribable polynucleotide molecule sequences may be introduced into any cell or organism such as algae cell, algae, fungal cell, fungi, bacterial cell, or insect cell. Preferred hosts and transformants include: fungal cells such as *Aspergillus*, yeasts, insects, bacteria and algae.

The transformed cell or organism is preferably prokaryotic, more preferably a bacterial cell, even more preferably a *Agrobacterium, Bacillus, Escherichia, Pseudomonas* cell, and most preferably is an *Escherichia coli* cell. Alternatively, the transformed organism is preferably a yeast or fungal cell. The yeast cell is preferably a *Saccharomyces cerevisiae, Schizosaccharomyces pombe*, or *Pichia pastoris*.

Having now generally described the invention, the same will be more readily understood through reference to the following examples which are provided by way of illustration, and are not intended to be limiting of the present invention, unless specified.

Each document, patent, and reference cited herein is herein incorporated by reference in its entirety.

The following examples are included to demonstrate preferred embodiments of the invention. It should be appreciated by those of skill in the art that the techniques disclosed in the examples that follow represent techniques discovered by the inventors to function well in the practice of the invention. However, those of skill in the art should, in light of the present disclosure, appreciate that many changes can be made in the specific embodiments that are disclosed and still obtain a like or similar result without departing from the spirit and scope of the invention, therefore all matter set forth or shown in the accompanying drawings is to be interpreted as illustrative and not in a limiting sense.

EXAMPLES

Example 1

Polynucleotide Molecule Identification and Cloning

Polynucleotide molecules were isolated from the eukaryotic translation initiation factor eIF4A genes of *Nicotiana tabacum, Arabidopsis thaliana*, and *Medicago truncatula* in order to identify elements able to affect transgene expression in all tissues of a dicot plant including the most sensitive reproductive organs such as anthers and meristem tissues. All the polynucleotide molecules were operably linked to the chloroplast transit peptide sequence, TS-At.SHKG-CTP2; the coding sequence for the glyphosate tolerant EPSPS gene isolated from *Agrobacterium tumefaciens* strain CP4, Cr-AGRtu.aroA, (U.S. Pat. No. 5,633,435, herein incorporated by reference); and the 3' nontranslated region of the ribulose bisphosphate carboxylase gene from *Pisum sativum*, T-PS.R-bcS2-E9 and used for glyphosate tolerance characterization.

The *Nicotiana tabacum* eIF4A-10 gene promoter, leader, and intron (referred to herein as P-Nt.eIF4A, L-Nt.eIF4A, and I-Nt.eIF4A, respectively) were cloned by designing primers to the publicly available genomic eIF4A-10 gene sequence available as GI:475215 Accession number X79008 through NCBI. Genomic DNA from *Nicotiana tabacum* was isolated and used to amplify the Nt.eIF4A-10 promoter, leader, and intron using PCR and the NteIF4A forward and reverse primers (provided as SEQ ID NO: 12 and 13, respectively). The sequence for the promoter P-Nt.eIF4A is provided as SEQ ID NO: 1; the sequence for the leader L-Nt.eIF4A is provided as SEQ ID NO: 2; the sequence for the intron I-Nt.eIF4A is provided as SEQ ID NO: 3. PCR products were then digested with SmaI and NcoI and cloned into a plasmid (pMON70501) digested with the same restriction enzymes to operably link the promoter, leader, and intron to the AROA gene (see for example PCT publication WO 2004/009761-A2, herein incorporated by reference). The subsequent construct (pMON70500) was screened by restriction enzymes digestion and sequencing to confirm that the correct sequence was present. A double cassette construct containing a second expression cassette was constructed by digesting pMON70500 with XmaI and sub-cloning in a cassette containing the 7Sa' promoter operably linked to the GUS transgene (from pMON13773 cut with NgoMIV and XmaI). The subsequent construct (pMON65396) was screened by restriction enzymes digestion.

The *Arabidopsis thaliana* eIF-4A1 gene promoter, leader, and intron (referred to herein as P-At.eIF4A, L-At.eIF4A, and I-At.eIF4A, respectively) were cloned by designing primers to the publicly available genomic eIF-4A1 gene sequence available as GI:14594801 Accession number AJ298137 through NCBI. Genomic DNA from *Arabidopsis thaliana* was isolated and used to amplify the At.eIF4A1 promoter, leader, and intron using PCR and the AteIF4A forward and reverse primers (provided as SEQ ID NO: 14 and 15, respectively). The sequence for the promoter P-At.eIF4A is provided as SEQ ID NO: 4; the sequence for the leader L-At.eIF4A is provided as SEQ ID NO: 5; the sequence for the intron I-At.eIF4A is provided as SEQ ID NO: 6. PCR products were then digested with NotI and NcoI and cloned into a plasmid (pMON65322) digested with the same restriction enzymes to operably link the promoter, leader, and intron to the AROA gene. The subsequent construct (pMON65395) was screened by restriction enzymes digestion and sequencing to confirm that the correct sequence was present.

The *Medicago truncatula* eIF-4A1 gene promoter, leader, and intron were identified by first identifying the best putative homologous gene in *Medicago truncatula*. Analysis was done using homology based sequence searches and phylogenetic reconstructions. The predicted protein sequences for known eIF-4A1 genes from *Nicotiana tabacum, Zea mays, Nicotinia plumbaginifolia*, and *Arabidopsis thaliana* were used to identify the best putative orthologous predicted protein sequence derived from *Medicago truncatula* genomic DNA. The genomic DNA sequence of this putative ortholog was then used to predict the gene's promoter, leader, and intron sequence for subsequent cloning.

The promoter, leader, and intron (referred to herein as P-Mt.eIF4A, L-Mt.eIF4A, and I-Mt.eIF4A, respectively) from the *Medicago truncatula* eIF-4A1 gene were cloned by designing primers to the identified genomic DNA sequence of interest. Genomic DNA from *Medicago truncatula* was isolated and used to amplify the Mt.eIF4A promoter, leader, and intron using PCR and three sets of MteIF4A forward and reverse primers: MtEIF4AF1 (SEQ ID NO: 16) and MtEIF4AR (SEQ ID NO: 19); MtEIF4AF2 (SEQ ID NO: 17) and MtEIF4AR; MtEIF4AF3 (SEQ ID NO: 18) and MtEIF4AR. Three variants of the promoter were thus created by truncating the promoter at the 5' end resulting in a 1941 bp promoter (referred to herein as P-Mt.eIF4A-1 and provided as SEQ ID NO: 7), a 1484 bp promoter (referred to herein as P-Mt.eIF4A-2 and provided as SEQ ID NO: 8), and a 1029 bp promoter (referred to herein as P-Mt.eIF4A-3 and provided as SEQ ID NO: 9). The three promoter variants were tested with the same leader and intron in order to directly compare their respective expression patterns. The sequence for the leader (referred to herein as L-Mt.eIF4A) is provided as SEQ ID NO: 10. The sequence for the intron (referred to herein as I-Mt.eIF4A) is provided as SEQ ID NO: 11. PCR products were then digested with NotI and PciI and cloned into a plasmid (pMON65322) digested with NotI and NcoI to operably link the promoter, leader, and intron to the AROA gene. Three subsequent constructs (pMON81504, pMON81505 and pMON81506) were screened by restriction enzymes digestion and sequencing to confirm that the correct sequence was present. Sequences and constructs referred to herein are summarized in Table 1 and 2, respectively.

TABLE 1

Sequences

| Element name | SEQ ID NO |
|---|---|
| P-Nt.eIF4A | 1 |
| L-Nt.eIF4A | 2 |
| I-Nt.eIF4A | 3 |
| P-At.eIF4A | 4 |
| L-At.eIF4A | 5 |
| I-At.eIF4A | 6 |
| P-Mt.eIF4A-1 | 7 |
| L-Mt.eIF4A | 10 |
| I-Mt.eIF4A | 11 |
| P-Mt.eIF4A-2 | 8 |
| L-Mt.eIF4A | 10 |
| I-Mt.eIF4A | 11 |
| P-Mt.eIF4A-3 | 9 |
| L-Mt.eIF4A | 10 |
| I-Mt.eIF4A | 11 |

TABLE 2

Constructs

| Construct | Regulatory Elements | Figure |
|---|---|---|
| pMON70500 | P-Nt.eIF4A/L-Nt.eIF4A/I-Nt.eIF4A/aroA | 1 |
| pMON65395 | P-At.eIF4A/L-At.eIF4A/I-At.eIF4A/aroA | 2 |
| pMON81504 | P-Mt.eIF4A-1/L-Mt.eIF4A/I-Mt.eIF4A/aroA | 3 |
| pMON81505 | P-Mt.eIF4A-2/L-Mt.eIF4A/I-Mt.eIF4A/aroA | 4 |
| pMON81506 | P-Mt.eIF4A-3/L-Mt.eIF4A/I-Mt.eIF4A/aroA | 5 |
| pMON65396 | P-Nt.eIF4A/L-Nt.eIF4A/I-Nt.eIF4A/aroA and P-Gm.7S'/GUS | — |
| pMON73663 | P-Gm.7S'/GUS and P-Nt.eIF4A/L-Nt.eIF4A/I-Nt.eIF4A/aroA | — |

TABLE 2-continued

Constructs

| Construct | Regulatory Elements | Figure |
|---|---|---|
| pMON73662 | P-At.eIF4A/L-At.eIF4A/I-At.eIF4A/aroA and P-Gm.7S'/GUS | — |
| pMON81509 | P-Mt.eIF4A-1/L-Mt.eIF4A/I-Mt.eIF4A/aroA and P-Gm.7S'/GUS | — |
| pMON81510 | P-Mt.eIF4A-2/L-Mt.eIF4A/I-Mt.eIF4A/aroA and P-Gm.7S'/GUS | — |
| pMON8151 | P-Mt.eIF4A-3/L-Mt.eIF4A/I-Mt.eIF4A/aroA and P-Gm.7S'/GUS | — |
| pMON26140 | P-FMV/L-Ph.DnaK/aroA | — |
| pMON20999 | P-FMV/L-Ph.DnaK/aroA | — |

Example 2

Promoter Characterization in *Arabidopsis thaliana*

Each gene of interest may be amplified from a genomic or cDNA library using primers specific to sequences upstream and downstream of the coding region. Transformation vectors are prepared to constitutively transcribe DNA in either sense orientation (for enhanced protein expression) or anti-sense orientation (for endogenous gene suppression) under the control of an enhanced Cauliflower Mosaic Virus 35S promoter (U.S. Pat. No. 5,359,142) directly or indirectly (Moore et al. PNAS 95:376-381, 1998; Guyer et al. Genetics 149: 633-639, 1998; International patent application NO. PCT/EP98/07577). The transformation vectors also contain a bar gene as a selectable marker for resistance to glufosinate herbicide.

The following abbreviations are used to describe the plants and seeds produced:

$R_0$=the original transgenic plant that was grown from a single transformed plant cell
$R_1$=the seed or plant progeny of the $R_0$ plant
$R_2$=the seed or plant progeny of the $R_1$ plant The transformation of *Arabidopsis* plants is carried out using the vacuum infiltration method known in the art (Bethtold et al. Methods Mol. Biol. 82:259-66, 1998). Seeds harvested from the plants, named as $R_1$ seeds, are subsequently grown in a glufosinate-containing selective medium to select for plants which are actually transformed and which produced $R_2$ transgenic seed.

A group of promoters were initially isolated and tested in *Arabidopsis thaliana* for their dicot expression pattern. Selected constructs including pMON70500 (containing P-Nt.eIF4A operably linked to the aroA transgene) and pMON65395 (containing P-At.eIF4A operably linked to the aroA transgene) were used to transform *Arabidopsis thaliana* ecotype Columbia by the floral dip method (N Bechtold et al. (1993) *CR Acad Sci Paris Sciences di la vie/life sciences* 316: 1194-1199 and S Clough et al. (1998) *Plant Journal* 16(6): 735-743). Analysis of glyphosate herbicide tolerance in transgenic *Arabidopsis* was used as an initial screen to identify promising promoters for subsequent analysis in other dicots.

Seeds from $R_0$ plants were harvested. Seeds from each cassette construct were sterilized and placed on 50 mM glyphosate agar media for selection of transformants. $R_1$ seedlings that germinated on glyphosate-containing agar were transferred to soil after 7 days.

Events from each construct were then analyzed for vegetative and reproductive tolerance to glyphosate. Plants transformed with pMON26140 (containing P-FMV operably linked to the aroA transgene) were used for comparison. This construct has been shown to provide 100% vegetative tolerance to glyphosate, but no reproductive tolerance, i.e. the glyphosate treated plants are not fertile. After three weeks plants in the rosette stage were sprayed with 24 ounces/acre (oz/A) or 128 ounces/acre of Roundup® Ultra herbicide. Each glyphosate treatment was done on at least 20 separate transgenic events per construct. Plants with vegetative damage were discarded. Plants treated with glyphosate that were morphologically similar to non-treated plants and which also formed siliques filled with seeds were considered tolerant. Data are provided in Table 3 below. Measurements are provided as the percentage of fertile glyphosate tolerant events out of the total events analyzed for each construct at each glyphosate dosage.

TABLE 3

Glyphosate tolerance in *Arabidopsis*

| Construct | Fertile Tolerant Events (% of events at 24 oz/A) | Fertile Tolerant Events (% of events at 128 oz/A) |
|---|---|---|
| pMON26140 | 0% | 0% |
| pMON65395 | 85% | 85% |
| pMON70500 | 48% | 34% |

From the initial group of promoters that were tested in *Arabidopsis*, the eIF4A-10 gene promoter, leader, and intron from *Nicoliana tabacum* (pMON70500) and the eIF-4A1 gene promoter, leader, and intron from *Arabidopsis thaliana* (pMON65395) were selected for further investigation. These were found to perform well in transformed *Arabidopsis* to provide glyphosate tolerance in both vegetative and reproductive tissues when compared to the control construct pMON26140.

Regulatory elements from the homologous gene in *Medicago truncatula* were tested in *Arabidopsis*. pMON81504 (containing P-Mt.eIF4A-1 operably linked to the aroA transgene), pMON81505 (containing P-Mt.eIF4A-2 operably linked to the aroA transgene), and pMON81506 (containing P-Mt.eIF4A-3 operably linked to the aroA transgene) were used to transform *Arabidopsis thaliana* by the floral dip method for in planta characterization of glyphosate tolerance. Plant transformation and glyphosate analysis were done as described above. Data are provided in Table 4 below. Measurements are provided as the percentage of fertile glyphosate tolerant events out of the total events analyzed for each construct.

TABLE 4

Glyphosate tolerance in *Arabidopsis*

| Construct | Tolerant Events (% of events at 24 oz/A) | Tolerant Events (% of events at 128 oz/A) |
|---|---|---|
| pMON26140 | 0% | 0% |
| pMON81504 | 33% | 30% |
| pMON81505 | 32% | 13% |
| pMON81506 | 14% | 10% |

All three constructs were found to perform well in transformed *Arabidopsis* to provide glyphosate tolerance in both vegetative and reproductive tissues when compared to the control construct pMON26140.

Example 3

Promoter Characterization in *Nicotiana tabacum* pMON70500, pMON26140, pMON73663 (a double cassette construct containing P-Gm.7S' operably linked to the GUS transgene and P-Nt.eIF4A operably linked to the aroA transgene), pMON65396 (a double cassette construct containing P-Nt.eIF4A operably linked to the aroA transgene and P-Gm.7S' operably linked to the GUS transgene), pMON73662 (a double cassette containing P-At.eIF4A operably linked to the aroA transgene and P-Gm.7S' operably linked to the GUS transgene), pMON81509 (a double cassette construct containing P-Mt.eIF4A-1 operably linked to the aroA transgene and P-Gm.7S' operably linked to the GUS transgene), pMON81510 (a double cassette construct containing P-Mt.eIF4A-2 operably linked to the aroA transgene and P-Gm.7S' operably linked to the GUS transgene), and pMON81511 (a double cassette containing P-Mt.eIF4A-3 operably linked to the aroA transgene and P-Gm.7S' operably linked to the GUS transgene) were used to transform *Nicotiana tabacum* cv. *Nicotiana samsun* by using the leaf disc method (R B Horsch, et al. (1985) Science 227:1229-1231 and R B Horsch, et al. (1987) *Plant Tissue and Cell Culture* pp. 317-329, Alan R. Liss, Inc.). Tobacco shoots were rooted in MS media ($R_0$ plants) and then transferred to soil. Tobacco plants were analyzed for glyphosate tolerance at the $R_0$ stage. After 38 days of growth in soil 30 to 35 plants per construct were sprayed with 96 ounces/acre Roundup® Ultra herbicide. Plants were scored for vegetative tolerance to glyphosate and for fertility. Plants with vegetative damage were discarded. Plants treated with glyphosate that were morphologically similar to non-treated plants and which also produced seeds were considered tolerant.

Transformation efficiency was measured and plants were analyzed for the percentage of events having reproductive tissue tolerance to glyphosate at 96 ounces/acre of Roundup® Ultra herbicide. Data are provided in Table 5 below.

TABLE 5

Glyphosate tolerance in Tobacco

| Construct | Fertile Tolerant Events (% of events at 96 oz/A) |
|---|---|
| pMON70500 | 28% |
| pMON65396 | 40% |
| pMON73663 | 7% |
| pMON73662 | 70% |
| pMON26140 | 0% |
| pMON81509 | 18% |
| pMON81510 | 9% |
| pMON26140 | 0% |

Example 4

Promoter Characterization in *Glycine max*

This example illustrates plant transformation useful in producing the transgenic soybean plants with constructs containing eIF-NCRE molecules of this invention, and the resultant production and identification of transgenic seed for transgenic soybean having an improved agronomic trait, i.e. improved nitrogen use efficiency, improved yield, improved water use efficiency and/or improved growth under cold stress as compared to control plants.

For *Agrobacterium*-mediated transformation, soybean seeds are germinated overnight and the meristem explants excised. The meristems and the explants are placed in a wounding vessel. Soybean explants and induced *Agrobacterium* cells from a strain containing construct plasmid DNA with the gene of interest cassette and a plant selectable marker cassette are mixed no later than 14 hours from the time of initiation of seed germination and wounded using sonication. Following wounding, explants are placed in co-culture for 2-5 days at which point they are transferred to selection media for 6-8 weeks to allow selection and growth of transgenic shoots. Trait positive shoots are harvested approximately 6-8 weeks post bombardment and placed into selective rooting media for 2-3 weeks. Shoots producing roots are transferred to the greenhouse and potted in soil. Shoots that remain healthy on selection, but do not produce roots are transferred to non-selective rooting media for an additional two weeks. Roots from any shoots that produce roots off selection are tested for expression of the plant selectable marker before they are transferred to the greenhouse and potted in soil.

pMON70500 and pMON20999 (containing P-FMV operably linked to the aroA transgene) were used to transform *Glycine max* by an *Agrobacterium* mediated method (see U.S. Pat. No. 6,384,301, herein incorporated by reference). Transformation efficiency was measured and then $R_0$ plants were selfed and advanced to the $R_1$ generation.

$R_1$ plants were tested for vegetative tolerance to glyphosate. For the $R_1$ evaluations, typically 48 seeds per event were planted and an ELISA analysis was performed to identify the positive transformants and to determine the segregation ratio. Plants were sprayed with 52 ounces/acre of Roundup Ultra-Max® herbicide at the V1 stage. Approximately one week post-spray the events were evaluated for chlorosis. Copy number and zygosity were also assessed. Other observations taken included: emergence, segregation, pod set (timing of), plant height, and maturity. Those events that had one copy of the transgene, no vector backbone, and vegetative glyphosate tolerance were advanced to the $R_2$ nursery to evaluate reproductive tolerance. $R_2$ plants were tested for reproductive tolerance to glyphosate. Plants treated with glyphosate that were morphologically similar to non-treated plants and which also produced seeds were considered tolerant. Data are provided in Table 6 below.

TABLE 6

Glyphosate tolerance in Soybean

| Construct | $R_1$ Events with Vegetative Tolerance | Fertile Tolerant Events (% of total events) |
|---|---|---|
| pMON70500 | 37% | 4% |
| pMON20999 | 55% | 0% |

Events containing the aroA transgene operably linked to the P-Nt.eIF4A promoter, leader, and intron showed acceptable transformation efficiency as well as good vegetative and reproductive tolerance to glyphosate in soybean when compared to the control. Four percent of the total events generated were found to have vegetative and reproductive tolerance in soybean to glyphosate in the $R_2$ generation.

Example 5

Promoter Characterization in *Gossypium hirsutum*

Construct pMON70500 was used to transform *Gossypium hirsutum* by *Agrobacterium*-mediated transformation methods (see PCT publication WO 00/36911, herein incorporated by reference).

First, $R_0$ plants were selfed to produce $R_1$ seed. $R_1$ seeds of this construct were planted in the greenhouse for multiple events. Glyphosate tolerance was analyzed using Roundup UltraMax® herbicide at a rate of 48 ounces/acre per application. Four applications were made at the 3, 6, 10, and 14 node stages respectively for a total of 192 ounces/acre of Roundup UltraMax® herbicide or 5.6 pounds of the acid equivalent of glyphosate per acre on each event. Events that demonstrated good vegetative tolerance (and segregated 3:1 according to Mendelian genetics) were advanced. Once the plants matured, they were mapped by recording boll retention at the first and second positions of the first five fruiting branches (highest possible score is 10). Plant mapping is a schematic or map of the plant noting where the fruit (boll) is being held or lost. It provides a good overall picture of how the plant is responding to stressors such as insect pressure, glyphosate sprays, or other stressors that may impact the ability of the plant to retain bolls, see for example U.S. Pat. No. 6,660,911, herein incorporated by reference. In this study the current commercial event mapped at 0 (n=4). Seven of the 9 events tested mapped slightly better than the current commercial event. Two of the events, Gh_S18179 and Gh_S18055, mapped 7.1 and 2.7 respectively (n=10), both far better than the current commercial event.

A second set of experiments was conducted, in which thirty $R_1$ seeds were planted in the greenhouse for multiple events. Glyphosate tolerance was analyzed using Roundup Ultra-Max® herbicide at a rate of 48 ounces/acre per application. Four applications were made at the 4, 8, 10 and 12-14 leaf stages. This was designed to give the plants a good dose of glyphosate at those growth stages we had identified as being stages or timings of higher plant sensitivity. As the effort progressed and outstanding tolerance from some of the events being tested was observed, the 48 oz/A rate was raised to 64 oz/A. Three experiments were performed with events from pMON70500. In total, 36 cotton events were screened for glyphosate tolerance from this NeIf/CP4 construct in cotton. Reproductive tolerance was based on boll retention. Two of these 36 events retained >50% of the first position bolls, which corresponds to a higher rate than the current commercial event.

Having illustrated and described the principles of the present invention, it should be apparent to persons skilled in the art that the invention can be modified in arrangement and detail without departing from such principles. We claim all modifications that are within the spirit and scope of the appended claims. All publications and published patent documents cited in this specification are incorporated herein by reference to the same extent as if each individual publication or patent application is specifically and individually indicated to be incorporated by reference.

We claim:

1. An isolated polynucleotide molecule having promoter activity, wherein said molecule is selected from the group consisting of:
   a. a DNA molecule comprising SEQ ID NO: 7; and
   b. a fragment comprising at least 95 contiguous nucleotide bases of SEQ ID NO: 7 having promoter activity.

2. The isolated polynucleotide molecule of claim 1 comprising SEQ ID NO: 7.

3. A polynucleotide construct comprising the isolated polynucleotide molecule of claim 1, wherein said isolated polynucleotide molecule is operably linked to a transcribable polynucleotide molecule.

4. The polynucleotide construct of claim 3, wherein the isolated polynucleotide molecule comprises the nucleic acid sequence of SEQ ID NO: 7.

5. The polynucleotide construct of claim 3, wherein said transcribable polynucleotide molecule is a gene of agronomic interest.

6. The polynucleotide construct of claim 3, wherein said transcribable polynucleotide molecule is a herbicide tolerance gene.

7. The polynucleotide construct of claim 6, wherein said herbicide tolerance gene is selected from the group consisting of genes that encode for phosphinothricin acetyltransferase, glyphosate resistant EPSPS, hydroxyphenyl pyruvate dehydrogenase, dalapon dehalogenase, bromoxynil resistant nitrilase, anthranilate synthase, glyphosate oxidoreductase and glyphosate-N-acetyl transferase.

8. A transgenic plant cell stably transformed with the polynucleotide construct of claim 3.

9. A transgenic plant stably transformed with the polynucleotide construct of claim 3.

10. The transgenic plant of claim 9, wherein the polynucleotide construct comprises SEQ ID NO: 7.

11. The transgenic plant of claim 9 or 10, wherein said plant is a monocotyledonous plant selected from the group consisting of wheat, maize, rye, rice, oat, barley, turfgrass, sorghum, millet and sugarcane.

12. The transgenic plant of claim 9 or 10, wherein said plant is a dicotyledonous plant selected from the group consisting of tobacco, tomato, potato, soybean, cotton, canola, sunflower and alfalfa.

13. A seed of said transgenic plant of claim 11, wherein said seed comprises said polynucleotide construct.

14. A seed of said transgenic plant of claim 12, wherein said seed comprises said polynucleotide construct.

15. A method of inhibiting weed growth in a field of transgenic glyphosate tolerant crop plants comprising: (i) planting transgenic plants transformed with an expression cassette comprising the isolated polynucleotide molecule of claim 1 operably linked to a polynucleotide molecule encoding a glyphosate tolerance protein and (ii) applying glyphosate to the field at an application rate that inhibits the growth of weeds, wherein the growth and yield of the transgenic crop plant is not substantially affected by the glyphosate application.

16. The method of claim 15, wherein said glyphosate tolerance protein is selected from the group consisting of a glyphosate resistant 5-enolpyruvylshikimate-3-phosphate synthase (EPSPS), a glyphosate oxidoreductase and a glyphosate-N-acetyl transferase.

17. The method of claim 15, wherein the transgenic plants are capable of tolerating an application rate ranging up to 256 ounces/acre.

18. The method of claim 15, wherein the application of glyphosate is at least once during the growth of the crop.

* * * * *